US009615806B2

United States Patent
Douglas et al.

(10) Patent No.: US 9,615,806 B2
(45) Date of Patent: Apr. 11, 2017

(54) METHOD AND APPARATUS FOR CREATION AND DISPLAY OF ARTIFACT-CORRECTED THREE DIMENTIONAL (3D) VOLUMETRIC DATA FROM BIPLANE FLUOROSCOPIC IMAGE ACQUISITION

(71) Applicants: David Byron Douglas, Winter Park, FL (US); Robert E. Douglas, Winter Park, FL (US)

(72) Inventors: David Byron Douglas, Winter Park, FL (US); Robert E. Douglas, Winter Park, FL (US)

(*) Notice: Subject to any disclaimer, the term of this patent is extended or adjusted under 35 U.S.C. 154(b) by 112 days.

(21) Appl. No.: 14/464,234

(22) Filed: Aug. 20, 2014

(65) Prior Publication Data
US 2016/0051217 A1 Feb. 25, 2016

(51) Int. Cl.
| | |
|---|---|
| G06T 15/00 | (2011.01) |
| A61B 6/00 | (2006.01) |
| G06T 19/00 | (2011.01) |
| A61B 6/02 | (2006.01) |
| G06T 7/00 | (2017.01) |

(52) U.S. Cl.
CPC ............ *A61B 6/5258* (2013.01); *A61B 6/022* (2013.01); *A61B 6/4014* (2013.01); *A61B 6/466* (2013.01); *A61B 6/481* (2013.01); *A61B 6/487* (2013.01); *A61B 6/501* (2013.01); *A61B 6/504* (2013.01); *A61B 6/507* (2013.01); *A61B 6/5205* (2013.01); *A61B 6/5241* (2013.01); *G06T 7/0067* (2013.01); *G06T 19/00* (2013.01); *G06T 2207/10121* (2013.01); *G06T 2210/21* (2013.01); *G06T 2210/41* (2013.01)

(58) Field of Classification Search
CPC ..... A61B 5/06; A61B 6/487; G06T 2207/301; G06T 2207/10121; G06T 2207/1012; G06T 19/00–19/20; H04N 21/8193; H04N 21/8355; H04N 2213/003
See application file for complete search history.

(56) References Cited

U.S. PATENT DOCUMENTS

| | | | | |
|---|---|---|---|---|
| 5,779,640 A | * | 7/1998 | Holley | ................ G01S 7/52046 600/447 |
| 6,461,040 B1 | * | 10/2002 | Mattson | ................... A61B 6/08 378/205 |
| 2006/0247521 A1 | * | 11/2006 | McGee | .................... A61B 5/06 600/434 |
| 2011/0038517 A1 | * | 2/2011 | Mistretta | .................. A61B 6/02 382/128 |

* cited by examiner

*Primary Examiner* — Charles Tseng
(74) *Attorney, Agent, or Firm* — Anderson Gorecki LLP

(57) ABSTRACT

A method and apparatus for creation and display of artifact-corrected three dimensional (3D) volumetric data from biplane fluoroscopic image acquisition is disclosed. Orthogonal images of a patient are obtained during an interventional medical procedure, the orthogonal images including an anterior-posterior (AP) image and a lateral image. A common coordinate system is established. The orthogonal images and the patient are plotted onto the common coordinate system. An intersection volume of the images is calculated. The data at each frame of the images are analyzed and a determination made regarding which x,z point of an AP image matches with which y,z point from a lateral image. An artifact correction process is performed and a resulting volumetric data set is plotted and displayed.

17 Claims, 23 Drawing Sheets

Representation of x-y plane, where z = 0

METHOD AND APPARATUS FOR CREATION AND DISPLAY OF ARTIFACT-CORRECTED THREE DIMENTIONAL (3D) VOLUMETRIC DATA FROM BIPLANE FLUOROSCOPIC IMAGE ACQUISITION

BACKGROUND

During an interventional procedure performed in a fluoroscopy suite, multiple sets of fluoroscopic images during contrast injection are acquired. A fluoroscopic unit has an x-ray tube, which emits x-rays and x-ray detector. Contrast material is injected into a blood vessel. Each set of fluoroscopic images obtained during an injection of contrast into a blood vessel is referred to as "run". Each run is performed with the patient as still as possible to prevent motion artifact. The initial image is prior to the injection of contrast material serves as a template for subtraction. Subsequent images after the injection of contrast material are obtained and a digital subtraction angiogram (DSA) is obtained. Each view (e.g. orthogonal Anterior-Posterior (AP) and Lateral) will have multiple images and the total number of images is based on the frame rate and the time of acquisition. For example, a frame rate of 15 images/second for a time of 6 seconds will have 90 images for each view or a total of 180 images. These DSA images are interpreted by the physician. The physician analyzes these images and can then make adjustments to the catheter(s), wire(s) or the positions of the fluoroscopy unit(s). Multiple sets of images are typically obtained throughout the procedure.

Orthogonal acquisition of data provides information in the superior-inferior direction (head-toe), the transverse (left-right or medial-lateral) direction and the anterior-posterior (front-back) direction. The images are displayed on two separate monitors. The physician can analyze each monitor and can use this information to track the course of a blood vessel or catheter as it moves through the patient.

SUMMARY

Conventional methods, such as those explained above, suffer from a variety of deficiencies. First, there is the inherent difficulty of analyzing two different images to understand precisely how the blood vessel or catheter moves through the body in three-dimensional space. It can be difficult to understand how the blood vessel moves in the superior-inferior, anterior-posterior and transverse directions. This interpretation is especially difficult when there are multiple structures overlapping. For example, in cerebral angiography it can be difficult to readily understand which branch of the middle cerebral artery on the Anterior-Posterior (AP) view correlates to its corresponding branch on the Lateral view.

There are several properties of a fluoroscopic image that makes interpretation difficult. These properties of a fluoroscopic image include magnification, displacement off the center of the x-ray beam, and changes in attenuation of the object based on its position within the body. The physician must be aware of these fluoroscopic properties and must appropriately compensate for the artifact when making decisions regarding diagnosis and/or treatment. An additional limitation is the fact that the physician must view two different images and mentally construct a map of the patient's unique anatomy. This current process of understanding the patient's unique anatomy can be extremely difficult to impossible when there are multiple overlapping blood vessels. When this occurs, another run of fluoroscopic images from different angles is frequently attempted.

Embodiments of the invention significantly overcome such deficiencies. This presently disclosed method and apparatus for the creation and display of artifact-corrected Three Dimensional (3D) volumetric data from biplane fluoroscopic image acquisition outlines a method to create an artifact corrected, volumetric data set, which can be presented in a 3D display. This can significantly help the physician in understanding of the anatomy. It will supplement the two separate displays and will create an overall improved diagnosis and treatment.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

In a particular embodiment of a method for providing the creation and display of artifact-corrected Three Dimensional (3D) volumetric data from biplane fluoroscopic image acquisition, the method includes obtaining orthogonal images of a patient during an interventional medical procedure, the orthogonal images including an anterior-posterior (AP) image and a lateral image. The method further includes establishing a common coordinate system and the plotting of the orthogonal images and the patient onto the common coordinate system. The method also includes calculating an intersection volume of the images and analyzing of the data at each frame of said images and determining which x,z point of an anterior-posterior (AP) image matches with which y,z point from a lateral image. Additionally the method requires performing an artifact correction process and plotting and displaying a resulting volumetric data set.

Other embodiments include a computer readable medium having computer readable code thereon for providing the creation and display of artifact-corrected Three Dimensional (3D) volumetric data from biplane fluoroscopic image acquisition. The computer readable medium includes instructions for obtaining orthogonal images of a patient during an interventional medical procedure, the orthogonal images including an anterior-posterior (AP) image and a lateral image. The computer readable medium further includes instructions for establishing a common coordinate system and the plotting of the orthogonal images and the patient onto the common coordinate system. The computer readable medium also includes instructions for calculating an intersection volume of the images and analyzing of the data at each frame of said images and determining which x,z point of an anterior-posterior (AP) image matches with which y,z point from a lateral image. Additionally the computer readable medium includes instructions for requires performing an artifact correction process and plotting and displaying a resulting volumetric data set.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides the creation and display of artifact-corrected Three Dimensional (3D) volumetric data from biplane fluoroscopic image acquisition as explained herein that when performed (e.g. when executing) on the processor, operates as explained herein within the computerized device to perform all of the method embodiments and operations explained herein as embodiments of the invention. Thus any computerized device that performs or is programmed to perform up processing explained herein is an embodiment of the invention.

Other arrangements of embodiments of the invention that are disclosed herein include software programs to perform the method embodiment steps and operations summarized above and disclosed in detail below. More particularly, a computer program product is one embodiment that has a computer-readable medium including computer program logic encoded thereon that when performed in a computerized device provides associated operations providing an attribute level change history as explained herein. The computer program logic, when executed on at least one processor with a computing system, causes the processor to perform the operations (e.g., the methods) indicated herein as embodiments of the invention. Such arrangements of the invention are typically provided as software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as software and hardware, or as hardware and/or circuitry alone, such as within a data communications device. The features of the invention, as explained herein, may be employed in data communications devices and/or software systems for such devices.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DESCRIPTION

Figure 1:
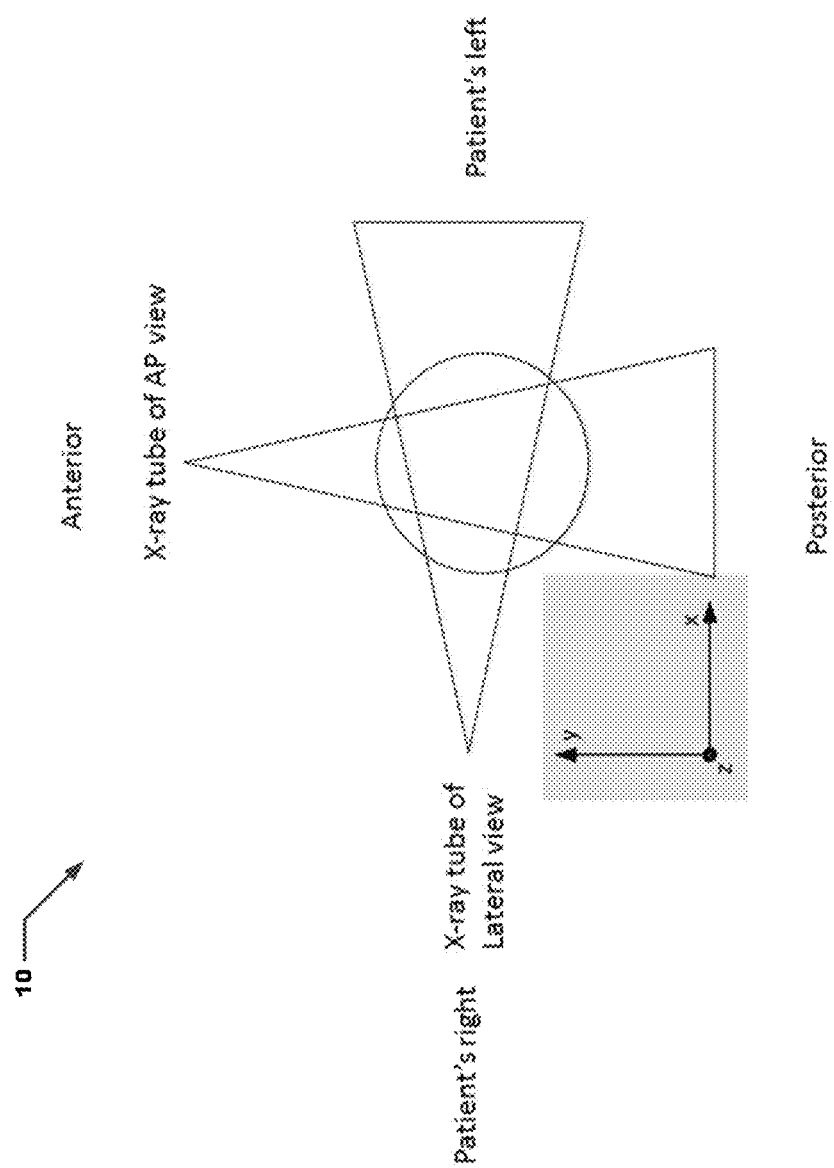
FIG. 1 shows biplane fluoroscopic units with x-ray beams and a coordinate system in accordance with a particular embodiment of the present invention.

The embodiments set forth below represent the necessary information to enable those skilled in the art to practice the invention and illustrate the best mode of practicing embodiments of the invention. Upon reading the following description in light of the accompanying figures, those skilled in the art will understand the concepts of the invention and recognize applications of these concepts not particularly addressed herein. It should be understood that these concepts and applications fall within the scope of the disclosure and the accompanying claims.

The preferred embodiment of the invention will now be described with reference to the accompanying drawings. The invention may, however, be embodied in many different forms and should not be construed as limited to the embodiment set forth herein; rather, this embodiment is provided so that this disclosure will be thorough and complete, and will fully convey the scope of the invention to those skilled in the art. The terminology used in the detailed description of the particular embodiment illustrated in the accompanying drawings is not intended to be limiting of the invention. In the drawings, like numbers refer to like elements.

There have been a recent advance in medical image processing technology (see U.S. Pat. No. 8,384,771 issued on Feb. 26, 2013 to David Byron Douglas), which describes a method and apparatus for displaying volumetric data in a true stereoscopic 3D perspective in a head display unit. There has also been a recent advance in the process of performing interventional procedures with precision external control of a catheter and wire based system (U.S. Patent Publication No. 20140039516 issued on Feb. 6, 2014 to David Byron Douglas).

With these new advances in image processing, image display and precision external control of a catheter and wire based system, there is now the impetus for conversion of biplane fluoroscopic images into volumetric dataset. The proposed patent could be used in combination with the afore mentioned patents which would create a combined method and apparatus with several major advantages. The conversion of biplane fluoroscopic runs into a volumetric data set provides the ability to view the data with 3D stereoscopic viewing with options to rotate the image, zoom and converge view point, which will result in improved detection and characterization of pathology. This improved visualization may obviate the need for additional runs and result in lower radiation dose and associated shorter procedure and anesthesia times, which would in turn result in both cost savings and less anesthesia risk. Finally, the precision control of a catheter-wire based system would be employed and would yield a more successful procedure technically with physician being outside of the interventional suite avoiding radiation exposure.

A summary of this invention's method for creation of an artifact corrected 3D volumetric dataset from biplane fluoroscopic image acquisition will now be described. While a particular process is described, similar processes can be performed to obtain this data set. The first step involves the establishment of a common coordinate system and the plotting of each fluoroscopy unit with associated x-ray tubes, x-ray beams, x-ray detectors and the patient onto the coordinate system. The second step involves the calculation the intersection volume of the x-ray beams. The third step involves the analysis of the data at each frame and applying an algorithm to determine which x,z point from the AP detector matches with which y,z point from the lateral detector. The fourth step involves performing an artifact correction process including correcting for magnification, distortion of object size based on the object distance from the center of the x-ray beam, attenuation effects and eliminating additional artifact such as that generated outside of the intersection volume. The fifth step involves performing additional calculations and pertinent assessments, such as caliber of vessels and flow rates (e.g., cm/sec). The sixth and final step involves plotting and displaying the resulting volumetric data set in a method such as that described in U.S. Pat. No. 8,384,771 with stereoscopic 3D viewing with options to view in cine format with rotation, zooming and converge view point.

The process of conversion of two biplane images into a 3D volumetric dataset involves the input of several parameters and several mathematical calculations. A sample set of mathematical calculations will be furnished; however, it should be noted that similar mathematical processes can be performed to accomplish this process. It should also be noted that the figures below are not drawn to scale.

In the first step a common coordinate system, such as the Cartesian coordinate system, encompassing both fluoroscopy units is established. The properties of the fluoroscopic units, such as position and x-ray beam width will be addressed below.

In the second step, the intersection volume of the x-ray beams is established. In biplane fluoroscopy, the physician would typically center the x-ray beams to intersect such that a similar region of interest within the patient can be viewed from different perspectives during the same injection. As such, the geometry of each of the biplane fluoroscopic units and the x-ray beams determine the intersection volume.

In the third step, the data at each frame is analyzed and an algorithm is applied to determine which x,z point from AP detector matches with which y,z point from Lateral detector. It should be noted that one example algorithm is given, but several variations of the algorithm could be applied to achieve a match between x,z points and y,z points. At each particular frame of a DSA image for both the AP and Lateral views, new points on the AP view detector and new points on the Lateral view detector will be analyzed and only certain points will be plotted (i.e., displayed) within the intersection volume. Assume the image subtraction on each fluoroscopic unit image is performed separately. Nominally, the AP unit will perform a subtraction image such that all initial x,z values are zero. Nominally, the Lateral unit will perform a subtraction image such that all initial y,z values are zero. Soon after this initial subtracted image, the contrast material will begin moving through the blood vessels and a set of biplane fluoroscopic images will be obtained. In order to define a point within the intersection volume, it must meet a set of criteria, which may include, but is not limited to the following: the z-value in the (x, z) point on the AP view detector must match and/or approximate the z-value in the (y, z) point on the Lateral view detector for a particular time interval or frame. Since new points appeared at the exact same point on the x, z plane and the x, y plane at the same frame, it is assumed that these points lie within the volume of interest. The time (particular frame) must match for each z-value. In addition, the attenuation value must also match. If all of these criteria are met, then x-values (for all x, z points) and all y-values (for all y,z points) will fill in the remaining coordinates to create x, y, z location for each density unit. In addition, vector analysis would aid in determining the x,z and y,z matches (FIG. 10-15). For example, we have assumed an arbitrary point "A" and we know that some small portion of fluoroscopy beams pass through this point and onto their respective displays. These small portions of the beams can be considered a x, z and a y, z vector for the AP and Lateral views, respectively. Where these vectors intersect is at point "A". Given the x,y,z coordinate space described above we can now plot "A" in 3D space. We do not know the gray shade of point "A", so we assign an arbitrary gray scale. Next, we want to be able to track both the flow of contrast material through the vascular system along with the location of the catheter. To do this, we digitally subtract the two images taken just prior to the injection of contrast material in order to start with a blank screen. Then as the contrast material begins to flow in the vascular system, the subtraction process will be continued and a spot will appear on both the AP and Lateral views. We then go through the vector process and can plot the initial voxel(s) containing the contrast material in the 3D coordinate system. Subsequent images will contain additional spots on the AP and Lateral views as the contrast material progresses through the vascular system. These additional spots will also be located through the vector process and plotted in the 3D system. Slight movement of the catheter will also appear on the respective displays and be located by the vector process and plotted in the 3D system. A color scheme is envisioned which could correspond to time of image (e.g., last voxels depicted in the 3D system could be darker than voxels obtain during earlier images). Alternatively, the scheme could correspond to measurement units such as contrast material velocity and/or volume. Finally, we depict the contrast flow over time as is currently viewed by the physician in order to give the reader some feeling of the difficulty in finding and correlating spots of potential interest and determining how to move the catheter in order to arrive at a desired location.

Numerous other methods for determining an x,z and y,z match can be performed. The size of a cluster of x,z points and the size of a cluster of y,z points can be analyzed and similar size clusters could be used to match. The attenuation of x,z points and y,z points can be analyzed to determine a match. The properties of flow rates could be used to aid in determining the x,z and y,z matches. Higher frame rates (e.g., 30 frames/sec) would enrich the data set and would aid in the processing. Subtraction of various combinations of frames could be performed to determine interval changes and enhance the matching of x,z and y,z data sets. In conclusion, this is a uniquely rich data set and multiple analysis methods could be employed for the creation of a volumetric data set for each frame in the DSA run.

Figure 15:
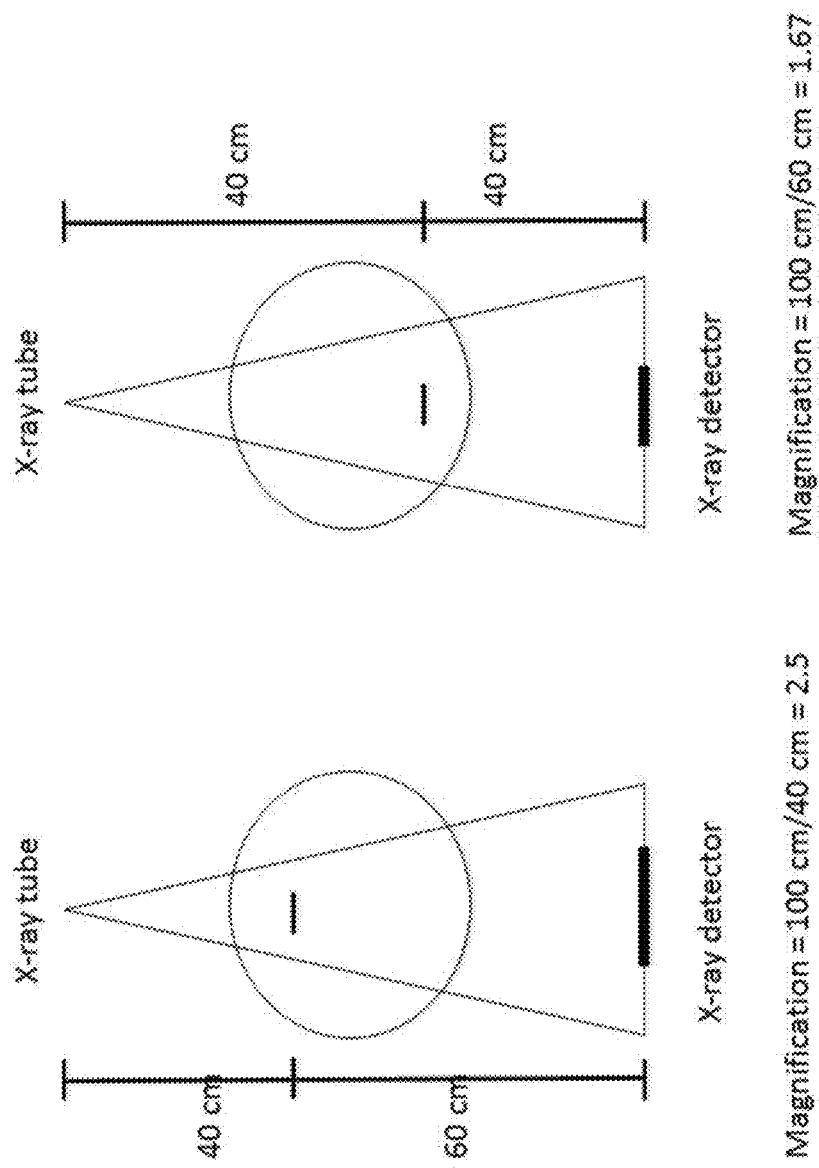
FIG. 15 illustrates the problem the radiologist has tracking from the AP view to the lateral view in accordance with a particular embodiment of the present invention.
Figure 16:
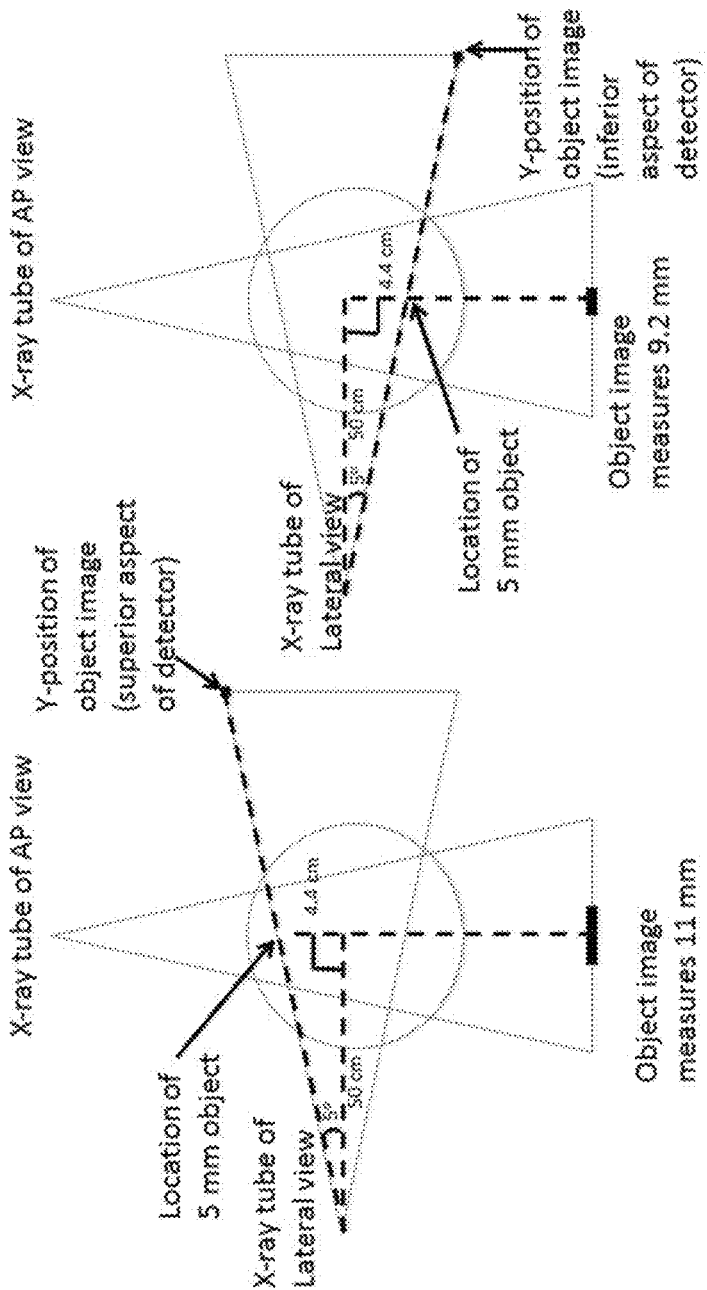
FIG. 16 illustrates the effects of magnification in fluoroscopy in accordance with a particular embodiment of the present invention.
Figure 17:
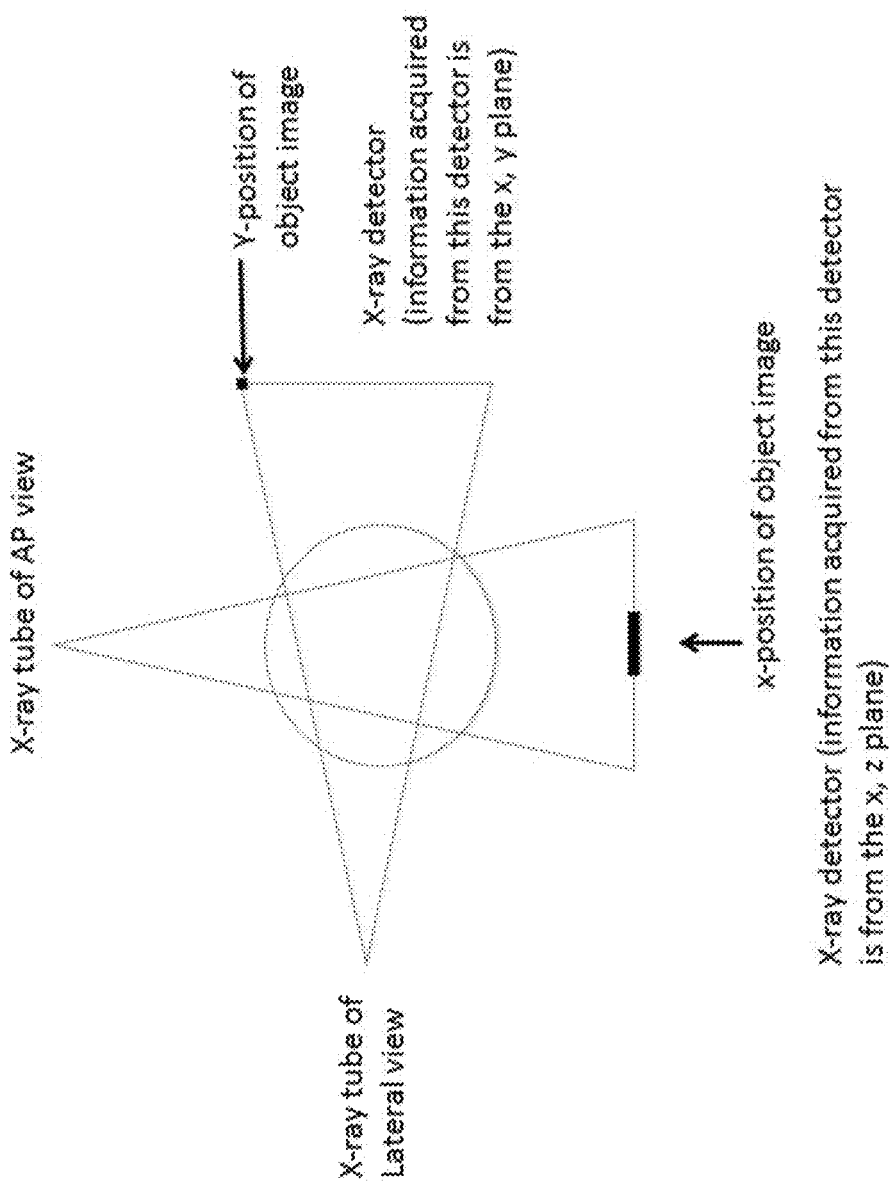
FIG. 17 illustrates a method to correct for magnification in accordance with a particular embodiment of the present invention.
Figure 18:
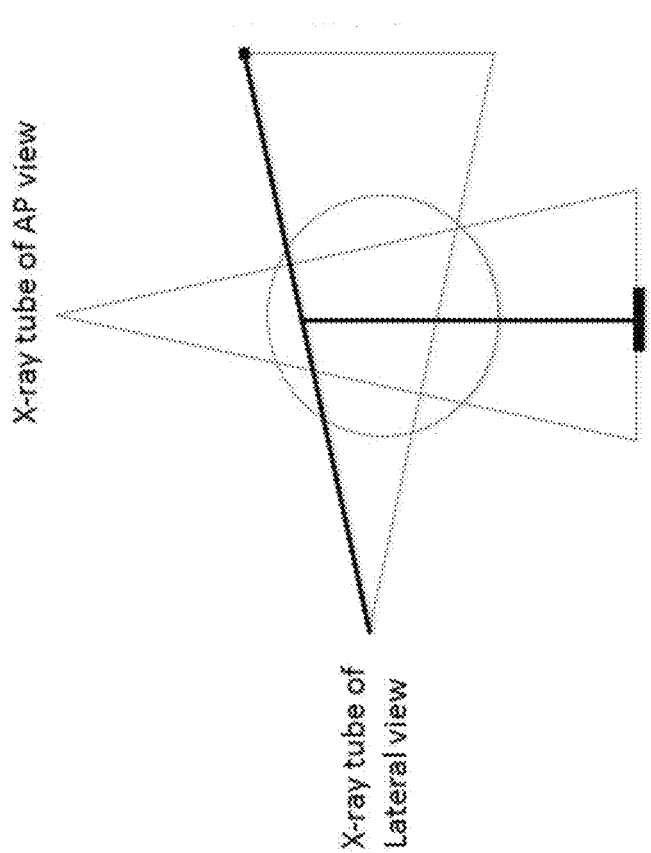
FIG. 18 illustrates a method to correct for magnification in accordance with a particular embodiment of the present invention.
Figure 19:
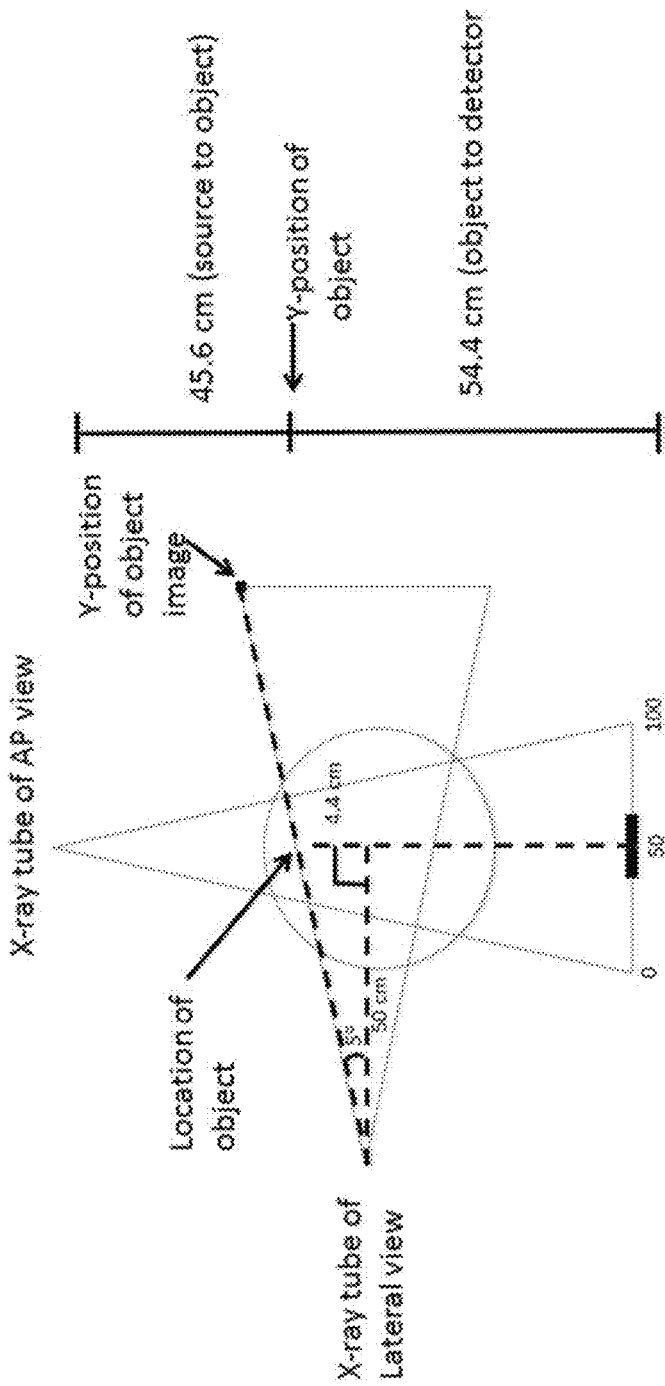
FIG. 19 illustrates a method to correct for magnification in accordance with a particular embodiment of the present invention.
Figure 20:
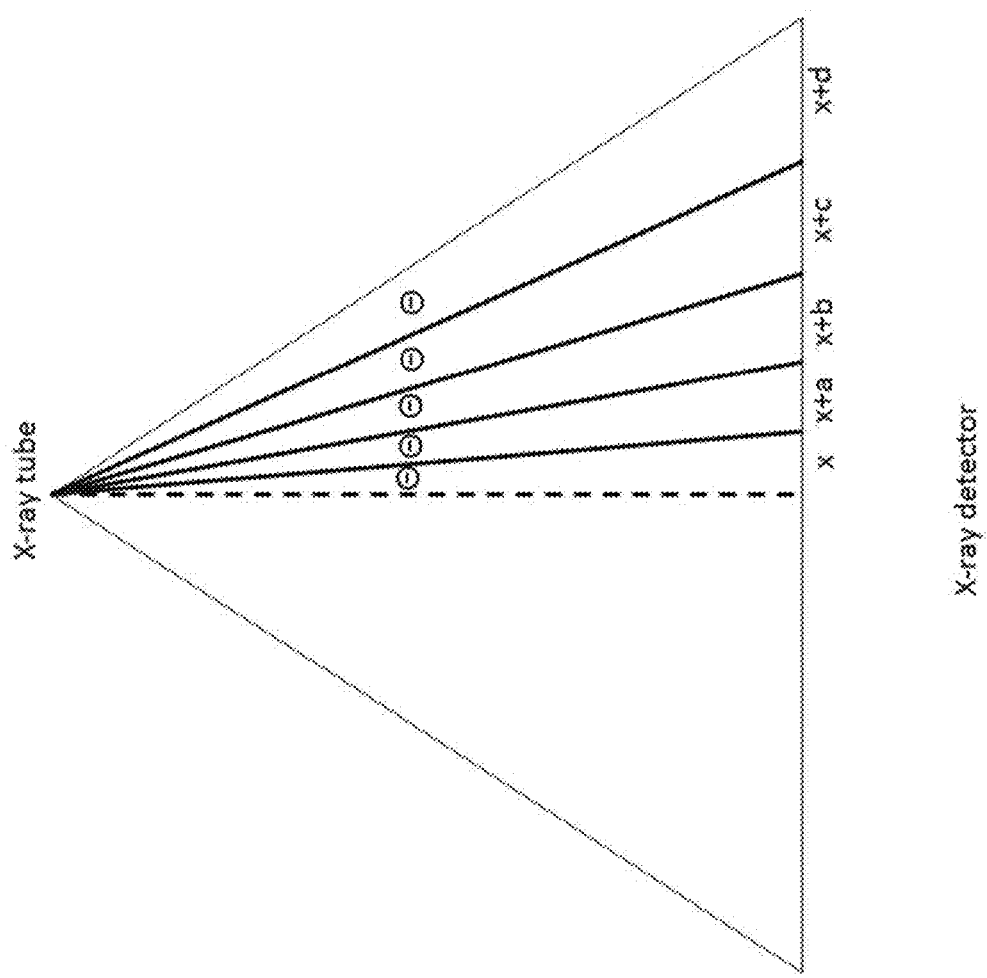
FIG. 20 illustrates a cross-section of x-ray beam in accordance with a particular embodiment of the present invention.
Figure 21:
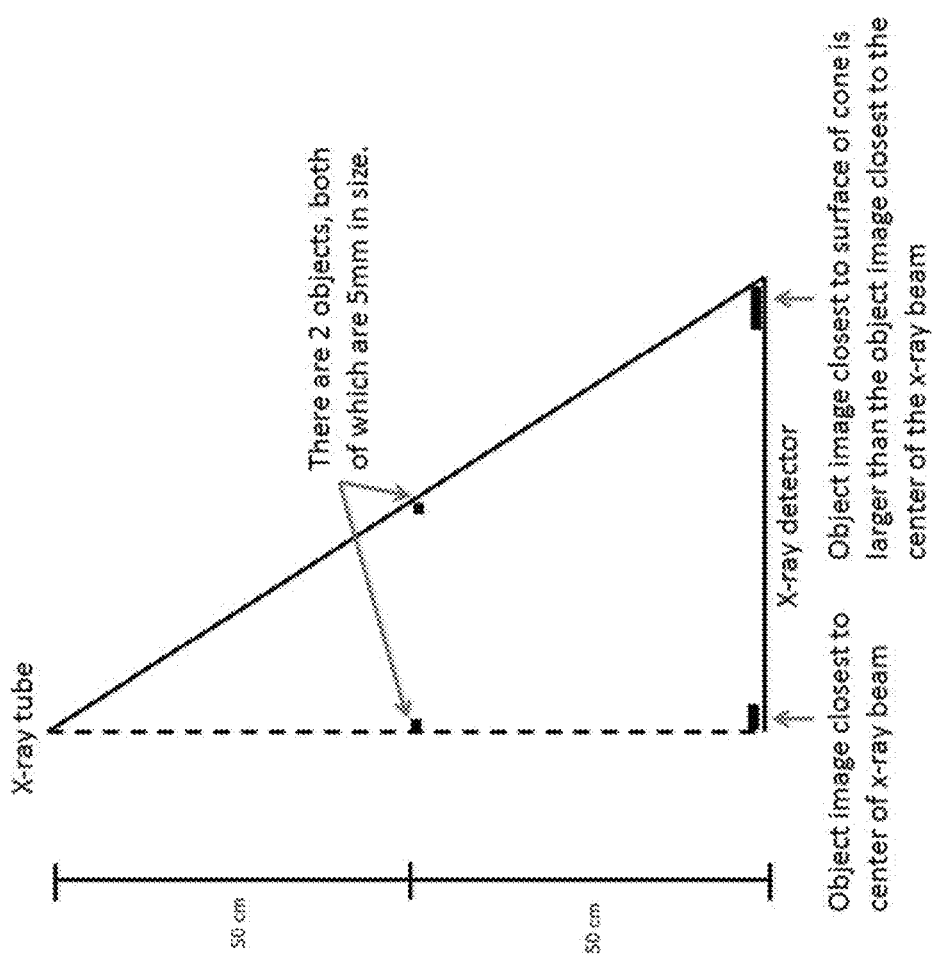
FIG. 21 illustrates a distortion based on distance of object from the center of the x-ray beam in accordance with a particular embodiment of the present invention.
Figure 23:
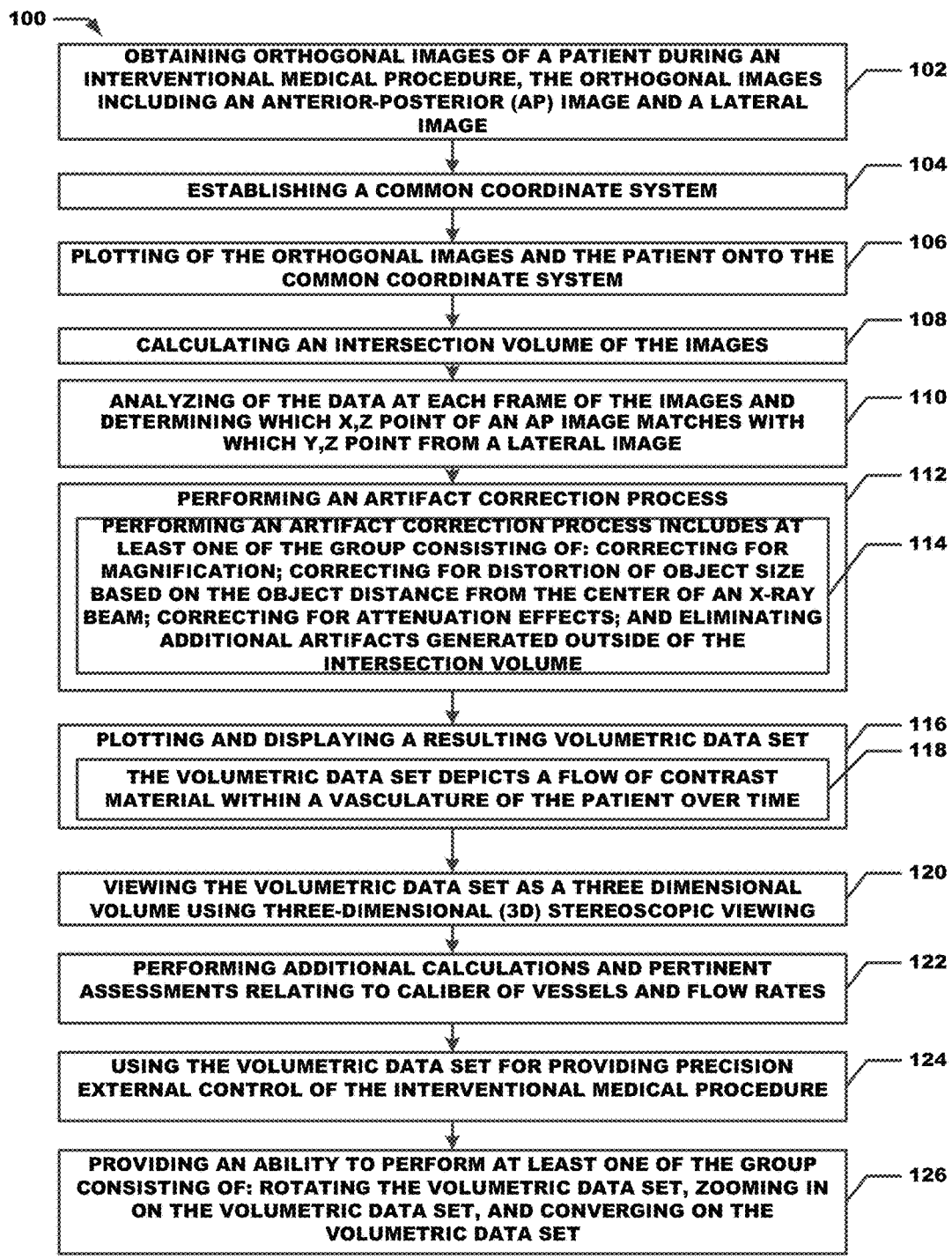
FIG. 23 depicts a flow diagram of a particular method for the creation and display of artifact-corrected three dimensional (3D) volumetric data from biplane fluoroscopic image acquisition.

In the fourth step, an artifact correction process would be performed including correcting for magnification, distortion of object size based on the object distance from the center of the x-ray beam, attenuation effects and eliminating additional artifact such as that generated outside of the intersection volume. Magnification is a source of artifact in fluoroscopy, which can limit the accuracy of diagnosis (FIG. 15). For example, if the neuroradiologist is measuring a small brain aneurysm in cerebral angiography, it is critical to know if the aneurysm is increasing in size over time. Slight changes in fluoroscopy technique over serial exams can affect the amount of magnification resulting in increases or decreases in size, which has major implications in medical management decisions. Given the process described in the third step of FIG. 1, the y-coordinate of an x,z cluster is known and this can be used to correct for the magnification effects on the size of the x,z cluster (FIG. 16-18). The same process could be performed in knowing the x-coordinate of a y,z cluster and this can be used to correct for the magnification effects on the size of the y,z cluster. Regarding the example of cerebral aneurysm follow up, this process of correction of magnification will result in more reliable comparison over time, which will lead to improved management decisions. Two examples of magnification correction are illustrated (FIG. 19). In a similar manner, the object size must be corrected based on the displacement off of the center line of the fluoroscopic image and the distance from the detector. The further away from the x-ray center line, the larger the distance that a given angle will subtend on the detector (FIG. 20). This larger distance will create distortion on the size of the object imaged (FIG. 21). A similar mathematical process can be performed to correct for the distortion based upon displacement from the center of an x-ray beam. In addition, the attenuation is altered based upon the object's location with the body. For example, at the tip of the catheter assume the material injected is full strength contrast (assume 100% contrast material injected). As the material travels through the vasculature, dilution occurs by the inflow of unopacified blood (i.e., blood not containing contrast material). Assume that the ratio of unopacified blood to contrast is 5:1. As this mixing continues, at some point it is no longer possible to track the flow of the contrast material since the gray scales become essentially indistinguishable for blood. The current process of independent interpretation of the attenuation (i.e., photons in a particular area on the detector) of an area of interest using only a single view (AP or Lateral) may be prone to error because attenuation is difficult to account for. This invention would also allow the calculation of the true attenuation of a voxel by a similar set of mathematical calculations by knowing the x, y, z location within the body as previously described. The x-ray beam would experience less attenuation as it passes through more dilute areas. This would show up as less photons in a corresponding area on the detector. Nominally, the density of the area of interest should correspond from the AP and Lateral views and similar values and would confirm that the area imaged is accurately represented, not artifact. Since the AP and Lateral views are susceptible to geometric effects and attenuation affects, the number of photons reaching a particular area on the detector is altered. Through mathematical calculations, the degree of alteration can be corrected for and the true density and relative dilution of contrast and relative flow of an area of interest can be calculated. Similar mathematical process can be performed to correct for attenuation effects. Furthermore, additional algorithms can be employed to reduce artifact created from outside of the intersection volume (FIG. 23).

Another example is to employ an algorithm such that all structures displayed must be contiguous. For example, if there was a string of contrast representing a vessel within the intersection volume and then suddenly a noncontiguous focus of contrast material appeared within the intersection volume, this could also be filtered out if this option were chosen and would be known not to represent a true blood vessel, which would show contiguous flow. Findings such as these would be expected to represent sources of artifact, such as motion. This is a rich data set and as described, multiple methods can be performed to eliminate artifact. It is also possible to superimpose images from multiple time frames so that the medical personnel replay and review the vascular structure wherein the contrast has moved over a period of time longer than a single particular frame.

In the fifth step, the analysis of the artifact-corrected volumetric data set is performed, such as calculation of the velocity of the blood (cm/sec) and flow rates (mL/sec). Given that all points are that are plotted in the intersection volume are corrected for magnification, displacement from the x-ray beam center line and corrected for attenuation, flow direction can be calculated in both velocity (e.g., cm/sec) as well as volume per unit time (e.g., mL/sec). Assume the leading edge of contrast represents the point within the blood vessel, which is furthest from the catheter along a particular branch. The velocity can be calculated as the distance between the (x,y,z) coordinate of the that the leading edge of contrast is at time point one to the (x,y,z) coordinate of the leading edge of contrast at time point two. For example, assume the initial location of the leading edge of contrast (10 cm, 10 cm, 10 cm) and that the next frame 0.125 sec later, the leading edge is at point (10 cm, 10 cm, 15 cm), the velocity can be calculated by 5 cm/0.125 sec or 40 cm/sec. This would be beneficial in assessment of whether a particular blood vessel has slow flow or fast flow compared with the rest of the blood vessels, which can be an indicator of pathology. The flow can also be calculated by the relative dilution after attenuation correction calculations. For example, if a total of 5 cc of contrast is administered over 1 second and there is a 5:1 dilution, then the flow rate in mL/sec is 25 mL blood/second. This additional information will aid in the interpretation of angiographic images and thus the patient's anatomy and detect any pathology. In addition, under this process, it is possible to depict the flow of contrast material as a function of time, thus giving the radiologist an accurate depiction of the vasculature and flow. This would help with diagnosis and help facilitate the next movements of wire and/or catheter. Flow rates can be displayed numerically or in a color coded map, such as faster flows are in red and slower flows are in blue.

In the sixth step, the resulting artifact-corrected volumetric data set is plotted. At this point, the data has been corrected for multiple sources of artifact including magnification, increasing displacement with increasing angles off the center line and altered attenuation based on flow, dilution and the location of the blood vessel within the body. The data could be displayed in gray scale or color maps with or without flow information. The data would nominally be displayed in a method such as that described in U.S. Pat. No. 8,384,771 with stereoscopic 3D viewing with options to view in cine format with rotation, zooming, converge, etc. Finally, after viewing the images, the physician could make a movement with his catheter and/or wire and this process be repeated.

In conclusion, combining this invention's method for creation of artifact-corrected 3D volumetric data from biplane fluoroscopic image acquisition with U.S. Pat. No. 8,384,771's method and apparatus of three dimensional viewing of images and U.S. Patent Publication No. 20140039516's method and apparatus of precision external control of interventional medical procedures will result in a new and improved system by which the physician can perform interventional medical procedures.

FIG. 1 shows the biplane fluoroscopic units with x-ray beams and coordinate system 10. Assume the position and angle of each fluoroscopic biplane unit are known. Assume that each fluoroscopic biplane unit is oriented perpendicular to one another such that one unit is obtaining a true AP view and the other unit is obtaining a true Lateral view. This is not required, but is assumed only for the purpose of the demonstrated calculations. Assume simultaneous acquisition of the AP view and the Lateral view images are synchronized in time, such that there are sets of images with both AP and Lateral views at time point as defined by the frame rate and the time of acquisition. Assume that the AP and Lateral views x-ray beams are fan-shaped defined by the collimation and intersect such that an intersection volume is created. Assume that the center beam of both the AP view fluoroscopy unit and the Lateral view fluoroscopy unit are in the same plane. Assume that the patient's area of interest, which is represented as the circle, is centered within the intersection volume of the x-ray beams. Assume a coordinate system with the x-axis being transverse (i.e., left to right across the patient), the y-axis being anterior to posterior and the z-axis being inferior to superior.

Figure 2:
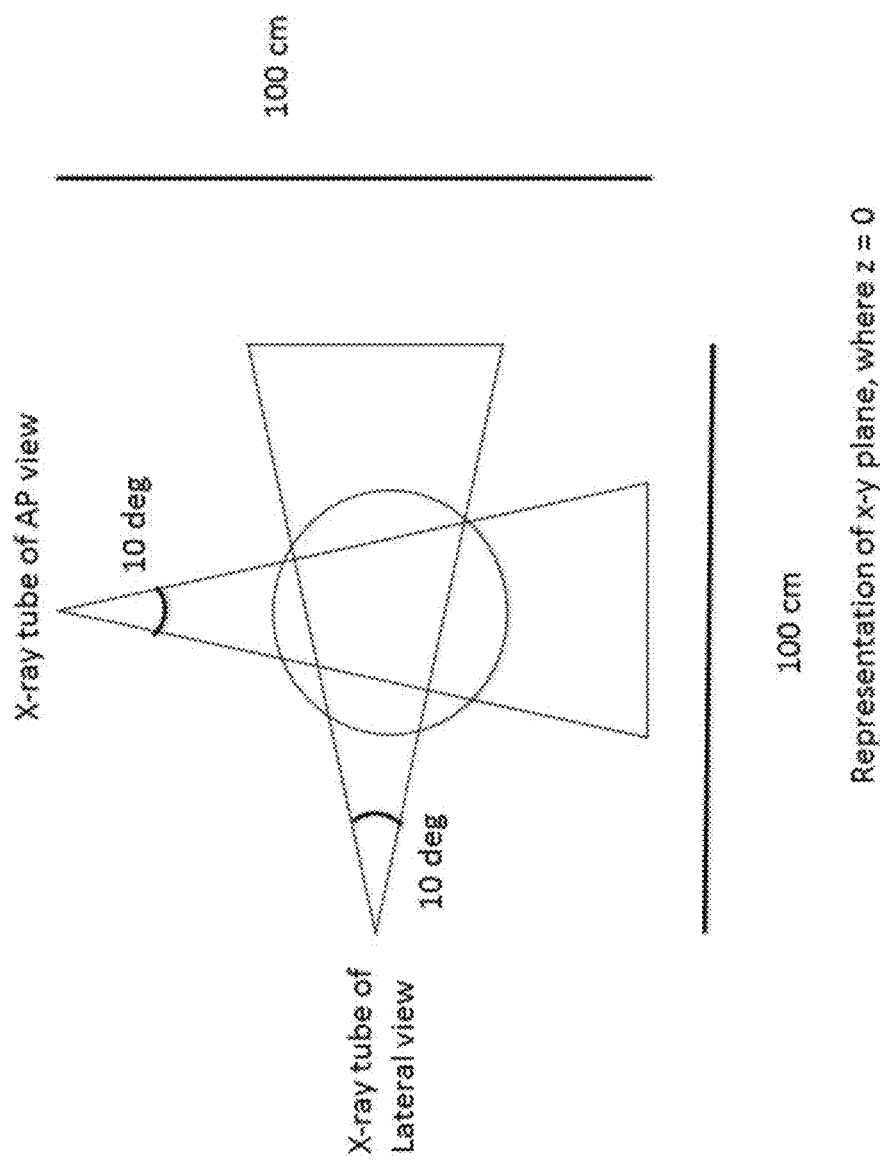
FIG. 2 shows properties of the biplane fluoroscopic units including distance and x-ray beam width in accordance with a particular embodiment of the present invention.

FIG. 2 shows properties of the biplane fluoroscopic units including distance and x-ray beam width. Assume that the distance from the x-ray tube to the detector is 100 cm for each x-ray fluoroscopy unit. Assume that the cone angle is 10 degrees. Assume that the x-ray tube has an angle between the center of the beam and the surface of the x-ray beam cone is 5 degrees (half of cone) with the total angular distance of each x-ray field of view of 10 degrees in the x-y plane where z equals 0.

Figure 3:
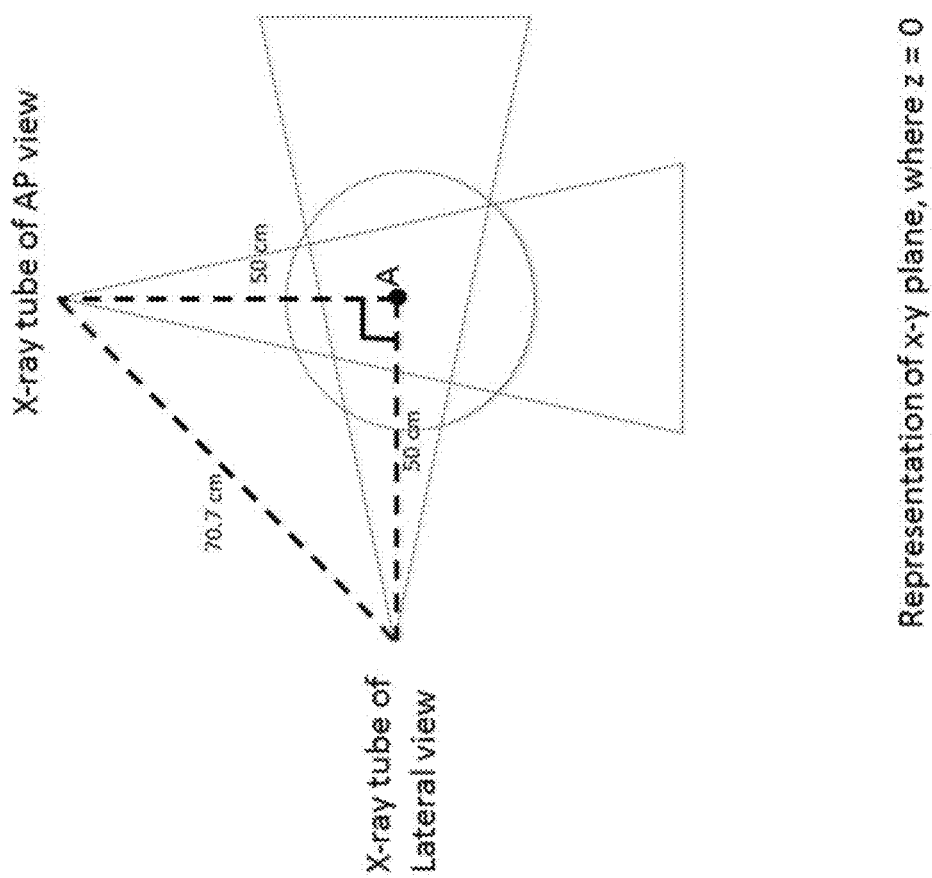
FIG. 3 shows the properties and calculation of the intersection volume wherein the x-ray beam volume from the AP fluoroscopic unit and the x-ray beam from the Lateral beam volume fluoroscopic unit share point A in accordance with a particular embodiment of the present invention.

FIG. 3 shows the properties and calculation of the intersection volume. The x-ray beam volume from the AP fluoroscopic unit and the x-ray beam from the Lateral beam volume fluoroscopic unit share point 'A.' Assume that "Point A" is 50 cm along the center of each x-ray beam is shared by both the AP view fluoroscopy unit and the Lateral view fluoroscopy unit and given this assumption, an isosceles triangle would be formed and the distance between the two x-ray tubes would represent the hypotenuse and be 70.7 cm away from one another in accordance with the Pythagorean theorem for a right triangle, $a^2+b^2=c^2$.

Figure 4:
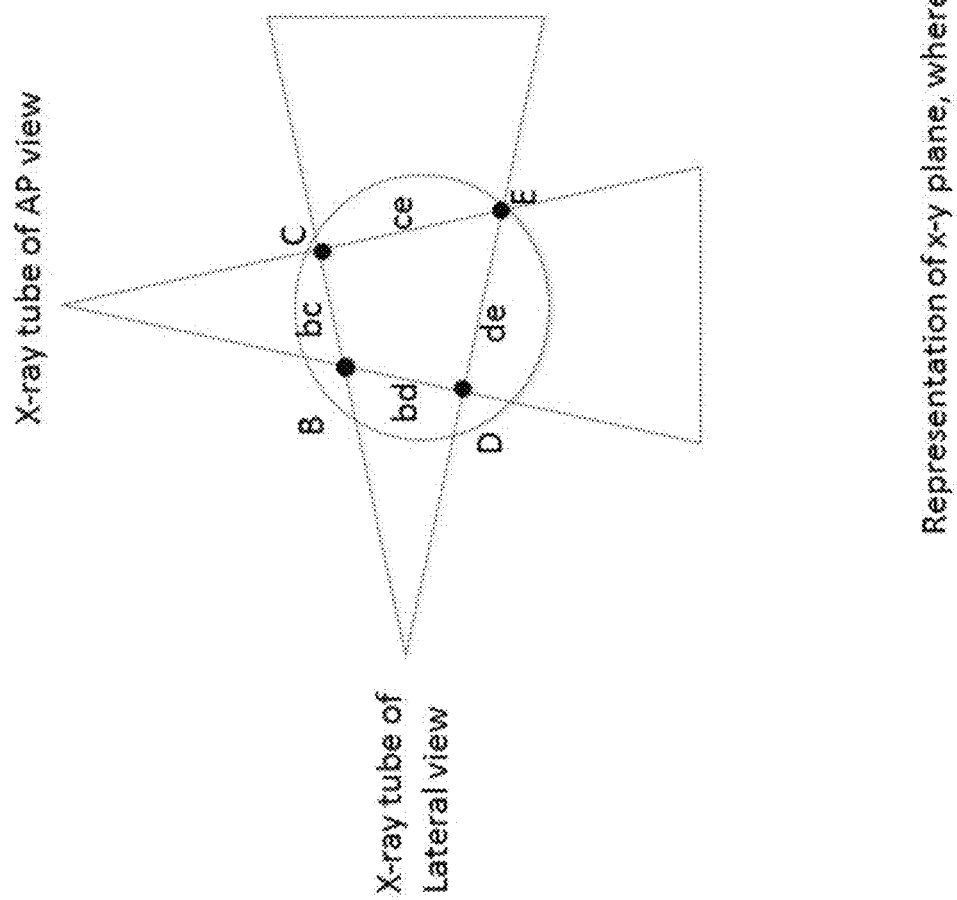
FIG. 4 shows the properties and calculation of the intersection volume wherein the boundaries of the intersection are illustrated in accordance with a particular embodiment of the present invention.

FIG. 4 shows the properties and calculation of the intersection volume. The boundaries of the intersection are illustrated. Assume that point "B" where the x-ray beams intersect at the anterior and right aspect of the patient. Assume that point "C" where the x-ray beams intersect at the anterior and left aspect of the patient. Assume that point "D" where the x-ray beams intersect at the posterior and right aspect of the patient. Assume that point "E" where the x-ray beams intersect at the posterior and left aspect of the patient. Assume that "bd" is the length between point "B" and point "D". Assume that "bc" is the length between point "B" and point "C". Assume that "de" is the length between point "D" and point "E". Assume that "ce" is the length between point "C" and point "E". Note that since symmetry is present in this case, bd" is equal to "bc" and "de" is equal to "ce".

Figure 5:
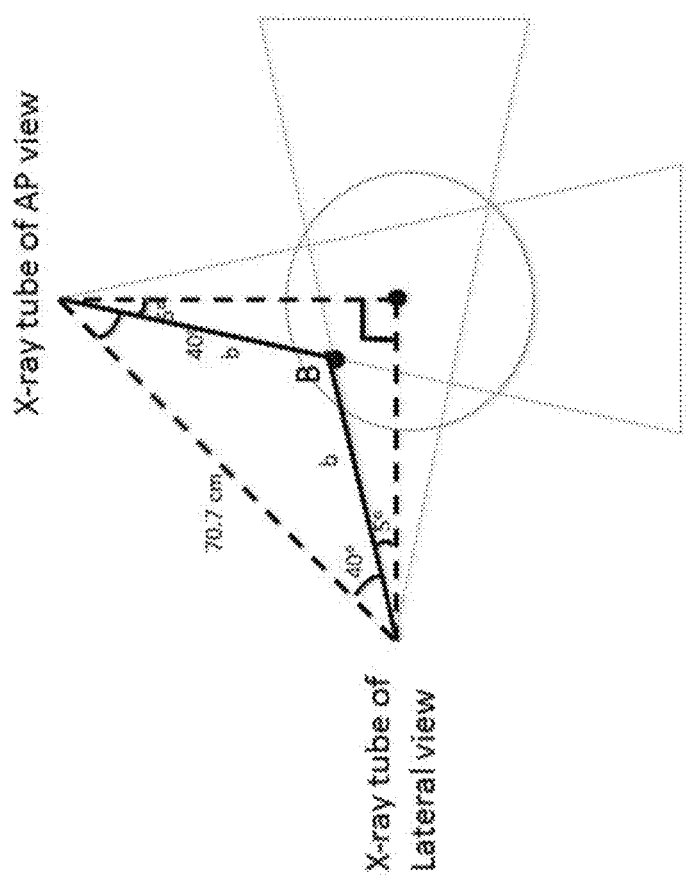
FIG. 5 shows the properties and calculation of the intersection volume wherein the boundaries of the intersection are illustrated in accordance with a particular embodiment of the present invention.

FIG. 5 shows the properties and calculation of the intersection volume. The boundaries of the intersection are illustrated. Assume that "b" is the length between the x-ray tubes and point "B". Length "b" calculated by the formula for a non-right triangle sin (40°)=b/70.7, such that "b" equals 45.4 cm.

Figure 6:
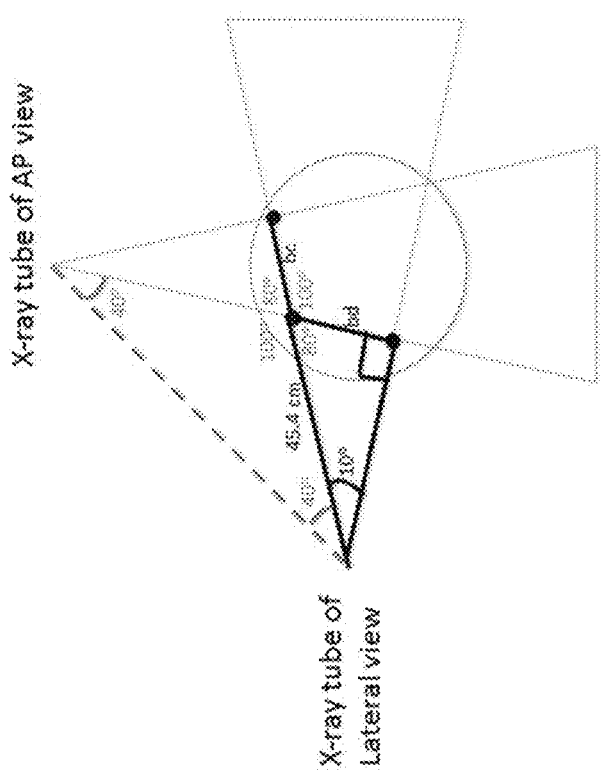
FIG. 6 shows the properties and calculation of the intersection volume wherein the boundaries of the intersection are illustrated in accordance with a particular embodiment of the present invention.

FIG. 6 shows the properties and calculation of the intersection volume. The boundaries of the intersection are illustrated. The length "bd" is one of the sides of a right triangle, such that "bd" is calculated by solving the equation sin (10°)=bd/45.4, such that "bd" equals 7.9 cm. Since length "bc" is equal to length "bd", then length "bc" is also 7.9 cm.

Figure 7:
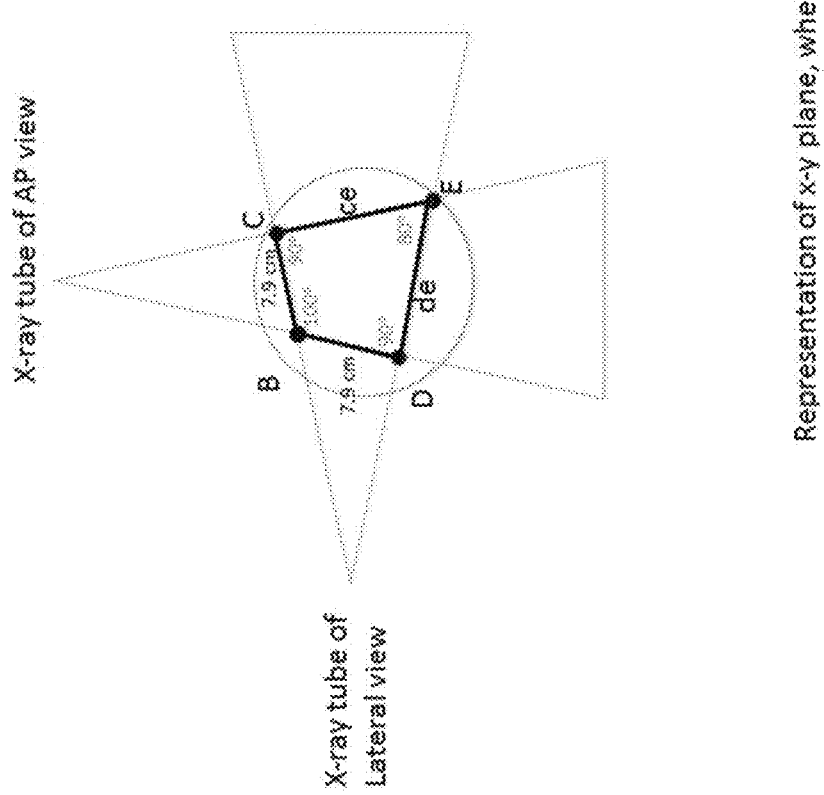
FIG. 7 shows the properties and calculation of the intersection volume wherein the boundaries of the intersection are illustrated in accordance with a particular embodiment of the present invention.

FIG. 7 shows the properties and calculation of the intersection volume. The boundaries of the intersection are illustrated. The next step is to calculate the internal angles of the parallelogram defined by "bc", "bd", "de" and "ce."

Figure 8:
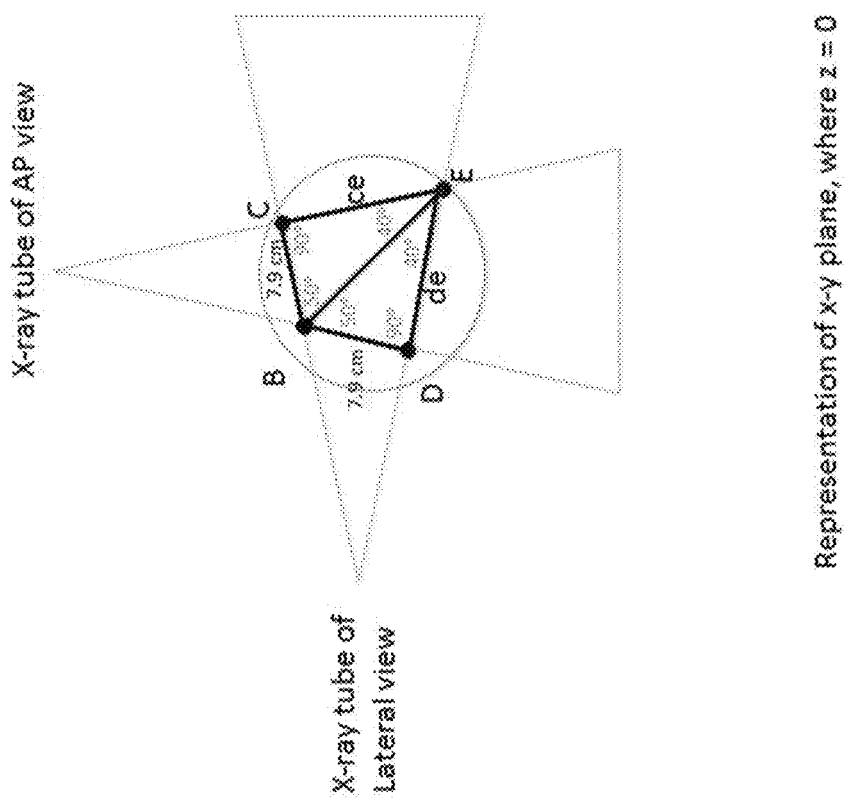
FIG. 8 shows the properties and calculation of the intersection volume wherein the boundaries of the intersection are illustrated in accordance with a particular embodiment of the present invention.

FIG. 8 shows the properties and calculation of the intersection volume. The boundaries of the intersection are illustrated. After the parallelogram is calculated, then a line is drawn from point "B" to point "E", which creates two triangles. Therefore, length "de" can be calculated by solving the equation tan (40)=7.9/de, such that length "de" equals 9.4 cm. Since length "de" is equal to length "ce", then length "ce" is also 9.4 cm.

Figure 9:
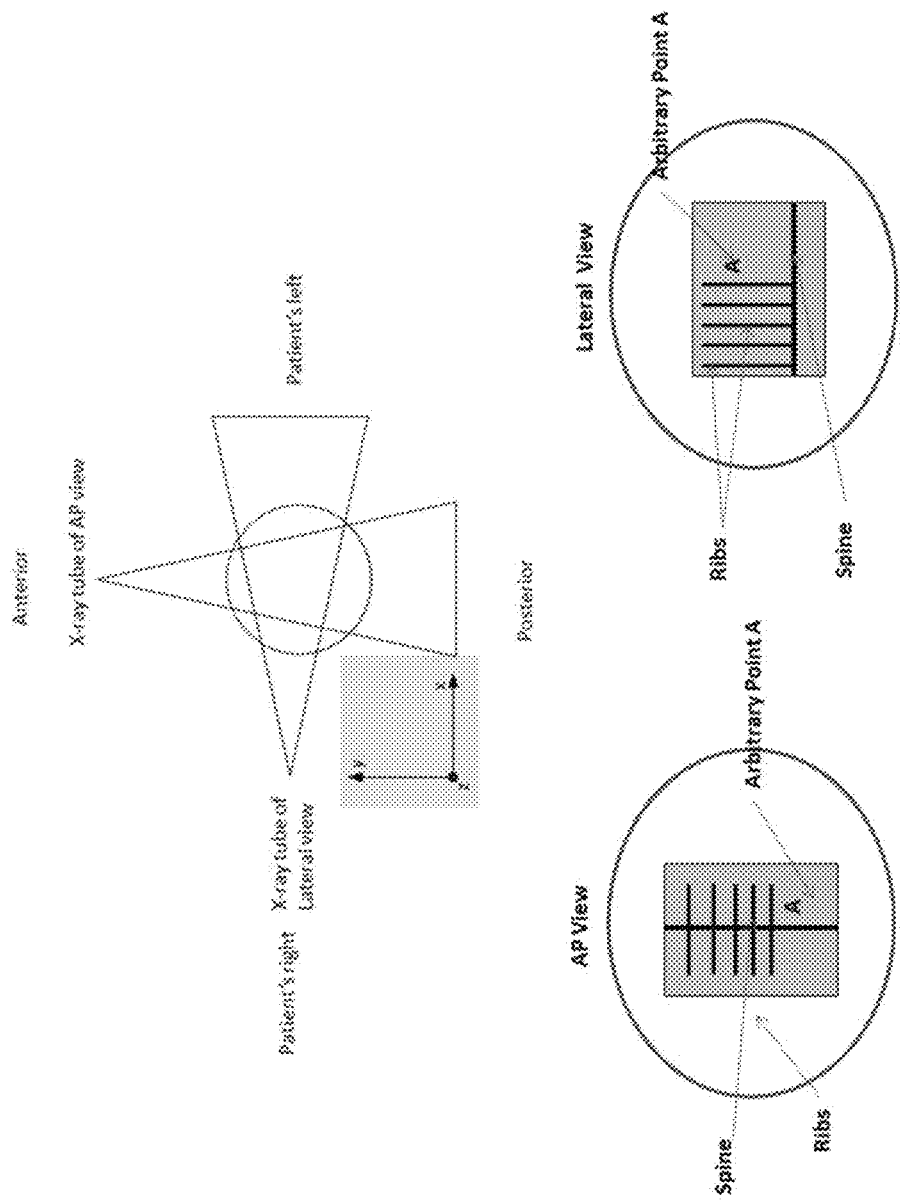
FIG. 9 shows the properties and calculation of the intersection volume wherein the boundaries of the intersection are illustrated in accordance with a particular embodiment of the present invention.

FIG. 9 shows the properties and calculation of the intersection volume. Based on the above assumptions and associated calculations, the intersection volume would have a cross-section of 7.9 cm×7.9 cm×9.4 cm×9.4 cm at the center of both the AP and Lateral x-rays. The adjacent cross-sections would depend on the collimation of each x-ray beam for the AP and Lateral views. A similar mathematical process can be used to determine the intersection area on adjacent slices; thus, intersection volume can be determined. Assume that the collimation for both the AP and Lateral views is circular, such that the angle between the center of the beam and the surface of the x-ray beam cone is 5 degrees. Note that square or rectangular collimation could be performed and this would result in a different shape of intersection volume. This process of defining the intersection volume can be performed with different coordinate systems.

FIG. 9 also shows the typical layout for biplane fluoroscopic image acquisition with associated coordinate system. Two X-ray machines are nominally employed which are positioned on the same x-y plane—one provides the anterior (AP) view and one provides the lateral view. X-ray beams are emitted simultaneously, nominally in a cone shape which is projected through the patient and onto a detector. The patient is positioned in a manner such that the volume of concern will be subtended by both AP and Lateral cones. The x-y plane will be considered a horizontal plane and the vertical direction will be the z direction. For convention, the transverse direction across the patient (from the patient's right side to the patient's left side) will be considered the "x-axis". For convention, the anterior-posterior direction across the patient (from the patient's front to the back) would be considered the "y-axis". For convention, the superior-inferior direction (from the patient's head to the patient's foot) would be considered the "z-axis".

Figure 10:
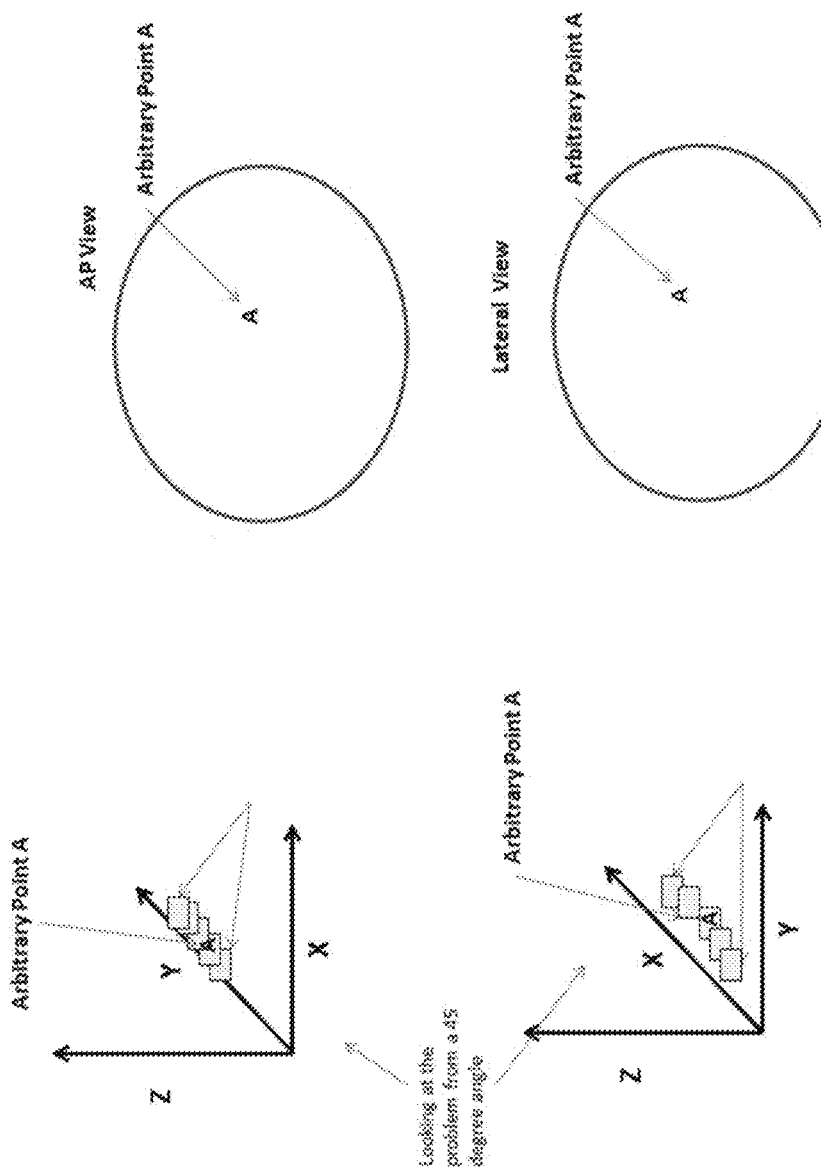
FIG. 10 shows a typical layout for the AP and Lateral views with a corresponding coordinate system depicted with an arbitrary point A in accordance with a particular embodiment of the present invention.

FIG. 10 depicts a set of voxels along a y-vector, one of which contains point "A"; similarly, a set of voxels along the x-vector, one of which contains point "A". In this figure we illustrate a patient undergoing biplane fluoroscopic image acquisition. For convenience, we have illustrated the coordinate system described with FIG. 10. We have shown example portions of the patient's body which would be imaged and available for review by medical personnel (e.g., radiologists). Importantly, we have illustrated an arbitrary point A. This arbitrary point will play a key role in subsequent figures. In this figure we illustrate a series of voxels that would be subtended by a small portion of the X-ray beam and would be detected as a single spot with a composite color (or gray shade) on the detector. For example, high density material such as contrast medium (e.g., Omnipaque 350) typically shows up on DSA (Digital Subtracted Angiogram) as dark gray/black on a white background. Within the patient there is the previously shown arbitrary point A. For the AP view, this set of voxels lie along the x-z; for the lateral view, the voxels lie along the y-z plane. Note that these planes are orthogonal in this example. The particular spot on the AP detector containing arbitrary point A would show up as some shade of gray and would be based on the density at point A and the density of the tissue subtended by the portion of the x-ray beam that lies on the detector element, which contains point A. A similar process would occur for the lateral view. Also, shades of gray for the two views representing the composite of the voxels would not necessarily be the same. Multiple voxels along a "Y" vector yielding a single gray scale pixel on the AP view display. The voxel containing arbitrary point A shows up with the composite gray on the display. Multiple voxels along an "X" vector yielding a single gray scale pixel on the Lateral view display. The voxel containing arbitrary point A shows up with the composite gray on the display.

Figure 11:
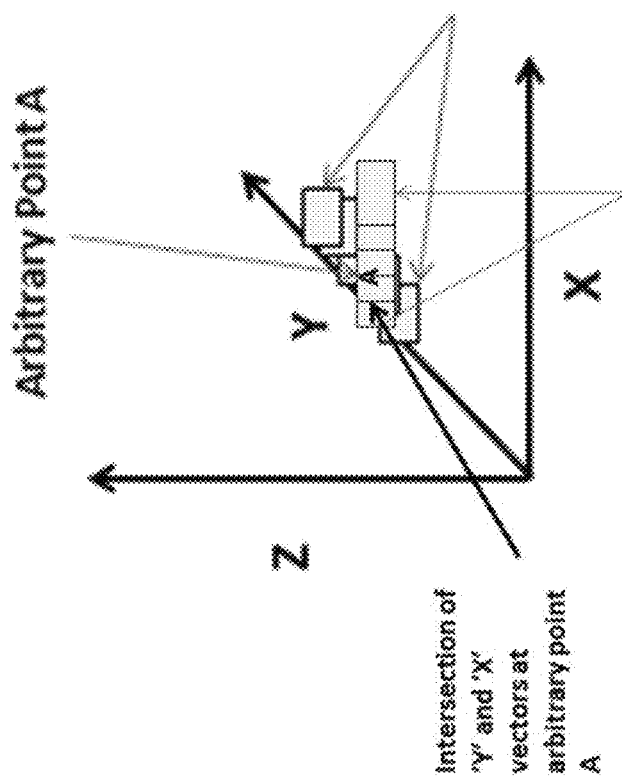
FIG. 11 depicts a set of voxels along a y-vector, one of which contains point "A"; similarly, a set of voxels along an x-vector, one of which contains point "A".

FIG. 11 shows is the intersection of the x-vector and y-vectors at arbitrary point "A". Here we have illustrated the set of voxels passing through arbitrary point A from both the AP and lateral views in a 3 dimension system. Point A could be shown in a 3D display system, but we still do not know what shade of gray to assign to it. Multiple voxels along a "Y" vector yielding a single gray scale pixel on the AP view display. The voxel containing arbitrary point A shows up with the composite gray on the display. Multiple voxels along an "X" vector yielding a single gray scale pixel on the Lateral view display. The voxel containing arbitrary point A shows up with the composite gray on the display.

Figure 12:
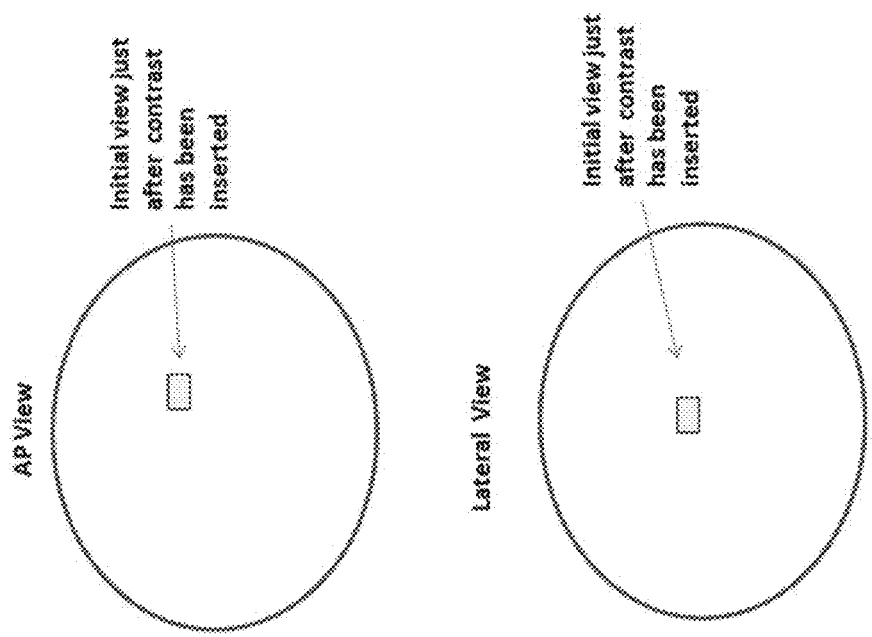
FIG. 12 shows is the intersection of the x-vector and y-vectors at arbitrary point "A" in accordance with a particular embodiment of the present invention.

FIG. 12 shows subtraction of the base images and just after the contrast has been injected. This step is invoked just prior to the injection of contrast. Clearly, if nothing has changed between collections of these two images, then the subtraction step will result in a blank screen. When the contrast is injected, and the subtraction step is repeated, something will have changed i.e., the appearance of small portion of contrast within the total image. Similar subtraction steps would be taking place with both the AP and Lateral views and a small portion of contrast would appear in the total lateral image. With the y-z coordinate and the x-z coordinate we can now convert those coordinates to a single voxel(s) in the 3 dimension x, y, z coordinate system. This spot would be given an arbitrary shade of gray. This would represent the first voxel(s) in the 3 dimensional data set and this data set would be independently recorded. After subtraction of the base images, and just after contrast fluid has been inserted ($t=t_1$), a single voxel will be visible in both the AP and the Lateral views. Based on the intersection of the "Y" vector and "X" vector from the previous chart, the X, Y, Z coordinates of the voxel will be available. This will constitute the beginning of building the composite volume viewed jointly by the AP and Lateral X-ray machines.

Figure 13:
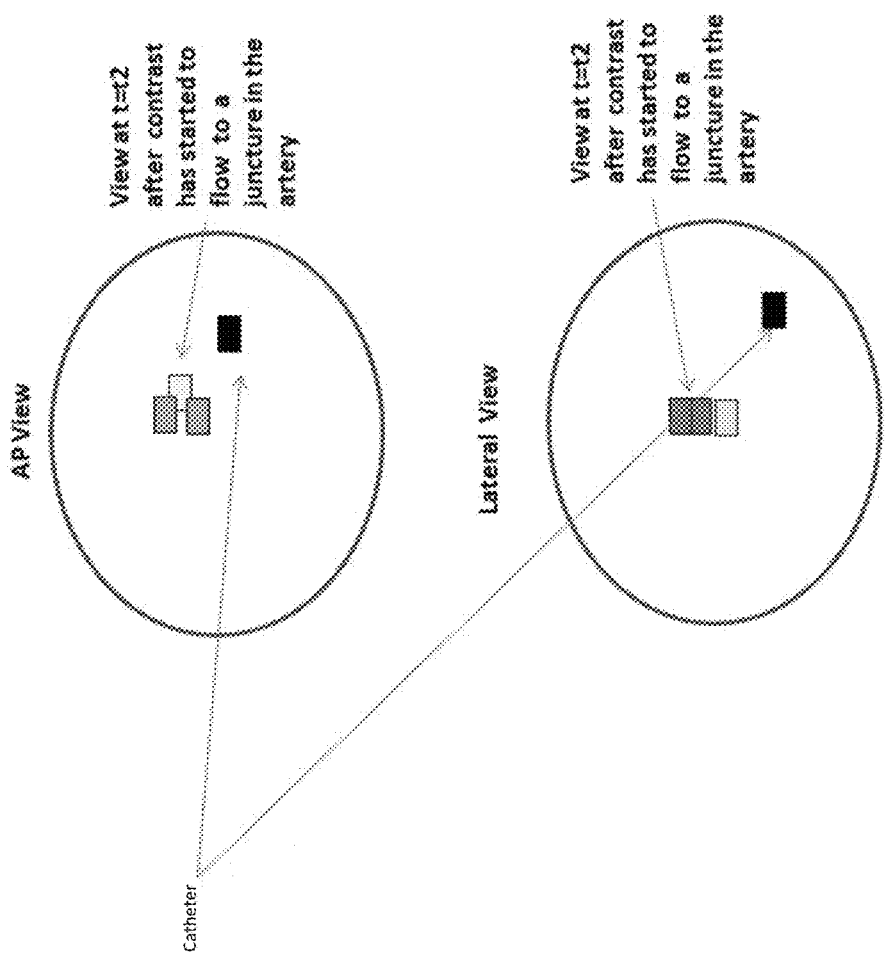
FIG. 13 shows subtraction of the base images and just after the contrast has been injected in accordance with a particular embodiment of the present invention.

FIG. 13 shows progress of contrast through the vascular system along with slight movement of the catheter, which is shown as the dark square. In this figure we illustrate the progression of the contrast through the artery system. The subtraction process described with FIG. 5 would continue and additional voxels with contrast would appear. These would be plotted and recorded in the 3 dimension data set.

In that the radiologist is interested in moving the catheter to some area of concern, a slight movement of the catheter would cause it to also appear through the subtraction process. The radiologist would be able to view the 3D data set using methods described in David Byron Douglas U.S. Pat. No. 8,384,771. This data can ultimately be displayed in the 3D volume in various gray-scales and/or colors, which could connote time differences and/or velocities and/or rates over time.

Slight movement of the catheter will cause it to become visible in the context of where the contrast is flowing. X, Y, Z coordinates can be computed for the catheter location. After contrast fluid has started to flow through the artery system, ($t=t_2$), additional voxels will be visible in both AP and Lateral views. After contrast fluid has started to flow thru the artery system, ($t=t_2$), additional voxels will be visible in both AP and Lateral Views. Based on the intersection of the 'Y' vectors and 'X' vectors, the X, Y, Z coordinates of these voxels will be available. This will continue building the composite volume viewed jointly by AP and Lateral X-ray machines and display the progress of the contrast fluid in the artery system. This data can ultimately be displayed in the 3D volume in various gray-scales and/or colors, which could connote time differences and/or velocities over time. Although the gray scales may be different in the AP and Lateral views due to machine differences, we know they represent the same voxels and an arbitrary gray scale could be assigned and displayed in the evolving volume.

Figure 14:
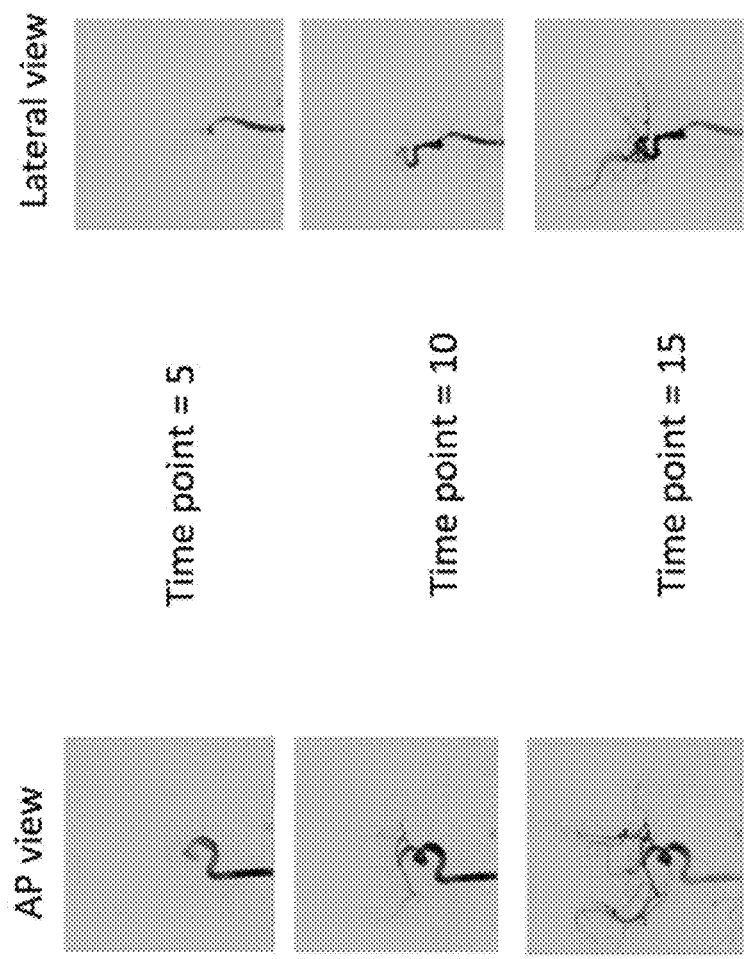
FIG. 14 shows progress of contrast through the vascular system along with slight movement of the catheter, which is shown as the dark square in accordance with a particular embodiment of the present invention.

FIG. 14 illustrates the problem the radiologist has tracking from the AP view to the lateral view. This figure illustrates the further progression of the contrast as it would be viewed by the current method. This highlights the current problems and challenges faced by the radiologist—specifically how to discern areas of overlap and how does one move the catheter through the maze. Illustrated are AP and Lateral views of a right Internal Carotid Artery injection demonstrates overlap of the Anterior Cerebral Artery and Middle Cerebral Artery branches. As contrast fluid continues to flow through the artery system, ($t=t_n$), additional voxels will be visible in both AP and Lateral views. Based on the intersection of the "Y" vectors and the "X" vectors, the X, Y, Z coordinates of these voxels will be available. This will continue building the composite volume viewed jointly by AP and Lateral X-ray machines and display the progress of contrast fluid in the artery system. This volume is what would be sent to the head display system described in U.S. Pat. No. 8,384,771.

FIG. 15 illustrates the effects of magnification in fluoroscopy. The circle represents the patient. The line within the circle represents the object. The thick line on the x-ray detector represents the object image. The patient, x-ray tube and x-ray detector are in the same position in both the left and the right diagrams. In the image on the left, the object is closer to the X-ray tube and there is more magnification. In the image on the right, the object is closer to the X-ray detector and there is less magnification. Magnification of an object can be calculated by the source to detector distance divided by the source to object distance. Assume source to detector distance is 100 cm. If the source to object distance is 40 cm, then the magnification is equal to 100 cm/40 cm or 2.5, which would mean the object image is 2.5 times the size of the object. If the source to object distance is 60 cm, then the magnification is equal to 100 cm/60 cm or 1.67, which would mean that the object image is 1.67 times the size of the object.

FIG. 16 illustrates method to correct for magnification. The object image seen on the AP view x-ray detector (x, z information) and is known to be magnified. Assume the x-position on the AP view detector is at the center of the AP view x-ray beam. Assume the y-position on the Lateral view detector is at the top (i.e. superior most portion) of the Lateral view x-ray beam. For the left image, magnification=100 cm/45.6 cm=2.19. Since the magnification factor can be calculated and the size of the object image known from the detector, the true size of the object of 5 mm can be calculated. For the right image, magnification=100 cm/54.4 cm=1.84. Since the magnification factor can be calculated and the size of the object image known from the detector, the true size of the object of 5 mm can be calculated.

FIG. 17 illustrates a method to correct for magnification. Since the y-position on the detector is at the superior most portion of the detector, the position of the object must arise from the top of the cone from lateral view. Since the x-position on the detector is centered on the AP detector, the position of the object must arise from the center of the cone from the AP view. The object image is seen in the AP view x-ray detector (x, z information) and is magnified. The object size can be calculated based on the y-position on the x-ray detector of the lateral view.

FIG. 18 illustrates method to correct for magnification. Since the x-position of the object image is at the center of the detector, the object is located along the center of the cone from the AP view. The angle from the center of the lateral view x-ray cone to the surface of the cone is 5°. Therefore, the height of the y-position can be calculated by solving $\tan(5°)$=(height of y-position)/50 cm. Thus, the source to object distance is 45.6 cm and the object to detector distance is 54.4 cm. Since the magnification factor can be calculated and the size of the object image known from the detector, the true size of the object can be calculated. The magnification can be calculated based on the y-position on the x-ray detector of the lateral view. Therefore, the true object size, which is magnification-corrected, can be calculated. Since the y-position of the object image is at the top of the detector, the object is located along the top of the x-ray beam cone from lateral view. Since the x-position of the object image is at the center of the detector, the object is located along the center of the cone from the AP view.

FIG. 19 illustrates two examples of magnification. Assume the x-position on the AP view detector is centered on the AP view detector. The diagram on the left demonstrates the object arising from the top of the cone from the lateral view, which would correspond to magnification of 2.19; thus, without a magnification correction applied, a 5 mm object would be measured on the AP view detector at 11 mm. With this invention's magnification correction, the AP view detector would measure 11 mm and would divide by the calculated magnification of 2.19 to calculate the magnification-corrected object size of 5 mm. The diagram on the right demonstrates the object arising from the bottom of the cone from the lateral view, which would correspond to a magnification of 1.84; thus, without a magnification correction applied, a 5 mm object would be measured on the Lateral view detector at 9.2 mm. With this invention's magnification correction, the AP view detector would measure 9.2 mm and would divide by the calculated magnification of 1.84 to calculate the magnification-corrected object size of 5 mm. Since the magnification factor can be calculated and the size of the object image known from the detector, the true size of the object can be calculated.

FIG. 20 shows a cross-section of X-ray beam demonstrated. The X-ray tube creates a fan-shaped X-ray beam with angle 10Θ as it travels toward the detector. The dashed line is the center of the X-ray beam. The fan-shaped x-ray beam is divided into 10 angles, each are equal in degrees and are labeled "Θ". The distance on the detector covered by the "Θ" closest to the center of the X-ray beam is "x". The distance covered by the adjacent "Θ" of X-ray beam is "x+a", which is larger than "x". Note that more degrees away from the center of the X-ray beam, the greater the distance on the detector, such that "x+d">"x+c">x+b">"x+a">"x".

FIG. 21 depicts a method for correction of distortion based on distance of object from the center of the x-ray beam. Assume that the distance between the x-ray tube and x-ray detector is 100 cm. Assume that this diagram demonstrates a cross-section of half of the x-ray beam. Assume the center of the x-ray beam is designated by the dotted line. Assume that the surface of the cone of the x-ray beam is marked by a solid line. Assume that there are two 5 mm objects located at 50 cm from the detector with one object located near the x-ray center line and the other object located near the side of the x-ray beam. Despite the fact that the objects are the same distance from the detector (i.e. 50 cm), the object image of the closer to the surface of the x-ray beam will be larger than the object image of the object near the x-ray center line. These objects are at different locations within the x-axis; thus, despite the same size of the objects, the object images will be different sizes. Mathematical analysis can be employed to determine correction factors for this distortion.

Figure 22:
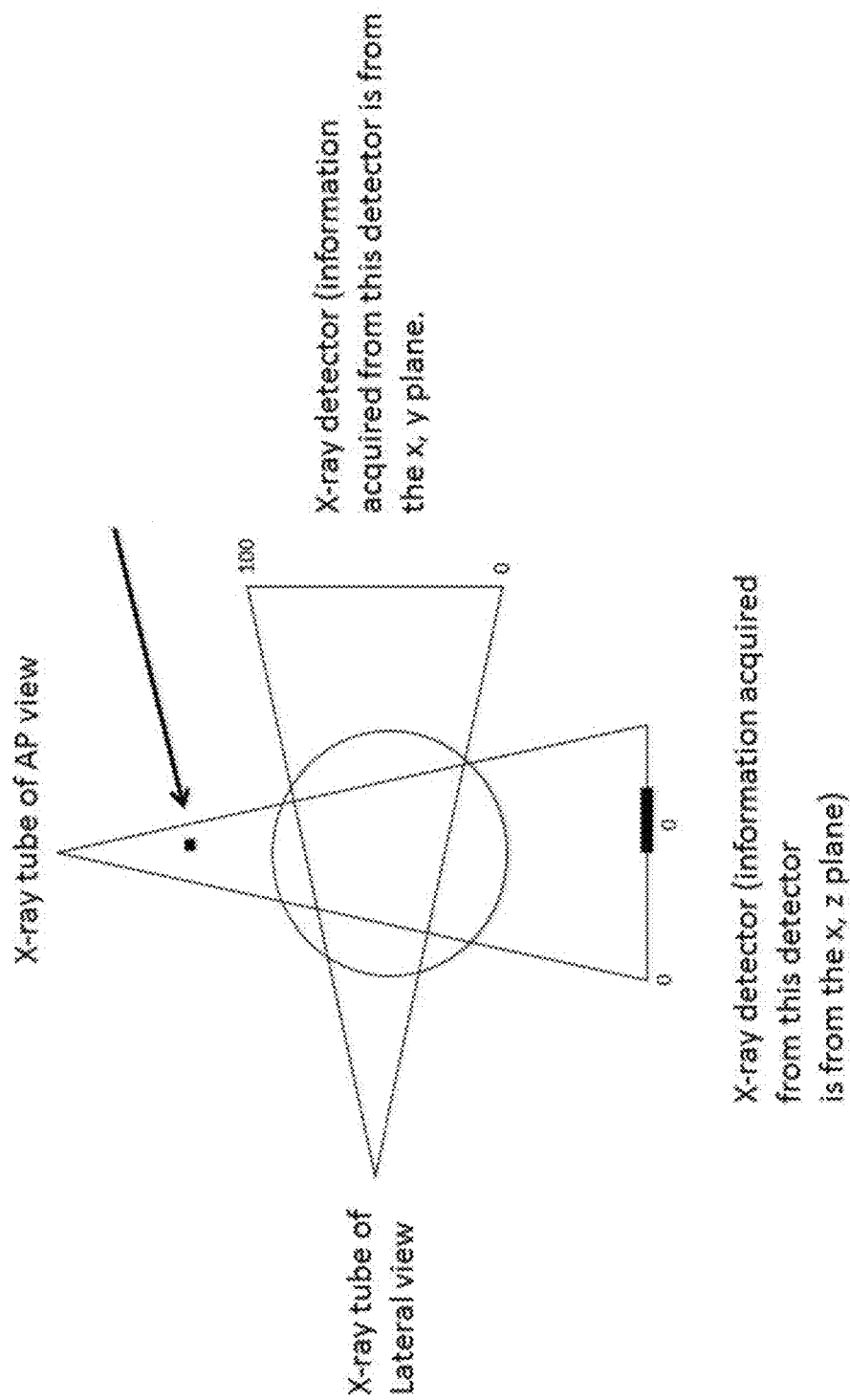
FIG. 22 illustrates a method to eliminate artifact arising outside of the intersection volume in accordance with a particular embodiment of the present invention.

FIG. 22 depicts a method to eliminate artifact arising outside of the intersection volume. As previously described, if there is a match, then the corresponding (x, y, and z) point will be displayed in the intersection volume. If there is not a match in the z-value in the (x, z) point on the AP view detector and the z-value in the (y, z) point on the Lateral view detector for a particular frame, then no point will be displayed in the intersection volume. For example, the AP view detector may show an object image on the x, z plane, but no corresponding object image on the Lateral view detector in the y, z plane. Therefore, this object would be determined to originate outside of the intersection volume and would not be displayed within the volume. This process of assuring that objects originate within the intersection volume will help correct for artifacts that originate from outside of the intersection volume.

A flow chart of the presently disclosed method is depicted in FIG. 23. The rectangular elements are herein denoted "processing blocks" and represent computer software instructions or groups of instructions. Alternatively, the processing blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Referring now to FIG. 23, a particular embodiment 100 of a method for creation and display of artifact-corrected three dimensional (3D) volumetric data from biplane fluoroscopic image acquisition is shown. Method 100 begins with processing block 102 which discloses obtaining orthogonal images of a patient during an interventional medical procedure, the orthogonal images including an anterior-posterior (AP) image and a lateral image.

Processing block 104 states establishing a common coordinate system. Processing block 106 recites plotting of the orthogonal images and the patient onto the common coordinate system. Processing block 108 discloses calculating an intersection volume of the images;

Processing block 110 states analyzing of the data at each frame of the images and determining which x,z point of an anterior-posterior (AP) image matches with which y,z point from a lateral image. Processing block 112 recites performing an artifact correction process. As shown in processing block 114, the performing an artifact correction process includes at least one of the group consisting of: correcting for magnification; correcting for distortion of object size based on the object distance from the center of an x-ray beam; correcting for attenuation effects; and eliminating additional artifacts generated outside of the intersection volume.

Processing block 116 discloses plotting and displaying a resulting volumetric data set. As shown in processing block 118, in a particular embodiment, the volumetric data set depicts a flow of contrast material within a vasculature of the patient over time. Processing block 120 states viewing the volumetric data set as a three dimensional volume using three-dimensional (3D) stereoscopic viewing.

Processing block 122 recites performing additional calculations and pertinent assessments relating to caliber of vessels and flow rates. Processing block 124 discloses using the volumetric data set for providing precision external control of the interventional medical procedure. Processing block 126 recites providing an ability to perform at least one of the group consisting of: rotating the volumetric data set, zooming in on the volumetric data set, and converging on the volumetric data set.

References to "a microprocessor" and "a processor", or "the microprocessor" and "the processor," may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor" or "processor" terminology may thus also be understood to include a central processing unit, an arithmetic logic unit, an application-specific integrated circuit (IC), and/or a task engine, with such examples provided for illustration and not limitation.

Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where such memory may be contiguous and/or partitioned based on the application. Accordingly, references to a database may be understood to include one or more memory associations, where such references may include commercially available database products (e.g., SQL, Informix, Oracle) and also proprietary databases, and may also include other structures for associating memory such as links, queues, graphs, trees, with such structures provided for illustration and not limitation.

References to a network, unless provided otherwise, may include one or more intranets and/or the internet, as well as a virtual network. References herein to microprocessor instructions or microprocessor-executable instructions, in accordance with the above, may be understood to include programmable hardware.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art.

Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD-ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

What is claimed is:

1. A method comprising:
   obtaining substantially simultaneous substantially orthogonal images of a patient from biplane fluoroscopic image acquisition during an interventional medical procedure, said substantially orthogonal images including an anterior-posterior (AP) image and a lateral image;
   establishing a common coordinate system;
   plotting of said substantially orthogonal images and the patient onto the common coordinate system;
   calculating an intersection volume of the images;
   analyzing of the data at each frame of said images and determining which x,z point of an anterior-posterior (AP) image matches with which y,z point from a lateral image;
   performing an artifact correction process, wherein said performing an artifact correction process includes at least one of the group consisting of: correcting for magnification; correcting for distortion of object size based on the object distance from the center of an x-ray beam; and correcting for attenuation effects; and
   plotting and displaying a resulting volumetric data set.

2. The method of claim 1 further comprising performing additional calculations and pertinent assessments relating to caliber of vessels and flow rates.

3. The method of claim 1 further comprising viewing said volumetric data set as a three dimensional volume using three-dimensional (3D) stereoscopic viewing.

4. The method of claim 3 further comprising using said volumetric data set for providing precision external control of the interventional medical procedure.

5. The method of claim 4 further comprising providing an ability to perform at least one of the group consisting of: rotating said volumetric data set, zooming in on said volumetric data set, and converging on said volumetric data set.

6. The method of claim 1 wherein said volumetric data set depicts a flow of contrast material within a vasculature of the patient over time.

7. A non-transitory computer readable storage medium having computer readable code thereon for creation and display of artifact-corrected Three Dimensional (3D) volumetric data from biplane fluoroscopic image acquisition, the medium including instructions in which a computer system performs operations comprising:
   obtaining substantially simultaneous substantially orthogonal images of a patient from the biplane fluoroscopic image acquisition during an interventional medical procedure, said substantially orthogonal images including an anterior-posterior (AP) image and a lateral image;
   establishing a common coordinate system;
   plotting of said substantially orthogonal images and the patient onto the common coordinate system;
   calculating an intersection volume of the images;
   analyzing of the data at each frame of said images and determining which x,z point of an anterior-posterior (AP) image matches with which y,z point from a lateral image;
   performing an artifact correction process, wherein said performing an artifact correction process includes at least one of the group consisting of: correcting for magnification; correcting for distortion of object size based on the object distance from the center of an x-ray beam; and correcting for attenuation effects; and
   plotting and displaying a resulting volumetric data set.

8. The computer readable storage medium of claim 7 further comprising instructions for performing additional calculations and pertinent assessments relating to caliber of vessels and flow rates.

9. The computer readable storage medium of claim 7 further comprising instructions for viewing said volumetric data set as a three dimensional volume using three-dimensional (3D) stereoscopic viewing.

10. The computer readable storage medium of claim 9 further comprising instructions for using said volumetric data set for providing precision external control of the interventional medical procedure.

11. The computer readable storage medium of claim 10 further comprising instructions for providing an ability to perform at least one of the group consisting of: rotating said volumetric data set, zooming in on said volumetric data set, and converging on said volumetric data set.

12. The computer readable storage medium of claim 7 wherein said volumetric data set depicts a flow of contrast material within a vasculature of the patient over time.

13. A computer system comprising: a memory; a processor;
a communications interface;
an interconnection mechanism coupling the memory, the processor and the communications interface; and
wherein the memory is encoded with an application providing creation and display of artifact-corrected Three Dimensional (3D) volumetric data from biplane fluoroscopic image acquisition, that when performed on the processor, provides a process for processing information, the process causing the computer system to perform the operations of:
obtaining substantially simultaneous substantially orthogonal images of a patient from the biplane fluoroscopic image acquisition during an interventional medical procedure, said substantially orthogonal images including an anterior-posterior (AP) image and a lateral image;
establishing a common coordinate system;
plotting of said substantially orthogonal images and the patient onto the common coordinate system;
calculating an intersection volume of the images;
analyzing of the data at each frame of said images and determining which x,z point of an anterior-posterior (AP) image matches with which y,z point from a lateral image;
performing an artifact correction process, wherein said performing an artifact correction process includes at least one of the group consisting of: correcting for magnification; correcting for distortion of object size based on the object distance from the center of an x-ray beam; and correcting for attenuation effects; and
plotting and displaying a resulting volumetric data set.

14. The computer system of claim 13 further comprising instructions for performing additional calculations and pertinent assessments relating to caliber of vessels and flow rates.

15. The computer system of claim 13 further comprising instructions for viewing said volumetric data set as a three dimensional volume using three-dimensional (3D) stereoscopic viewing.

16. The computer system of claim 15 further comprising instructions for using said volumetric data set for providing precision external control of the interventional medical procedure.

17. The computer system of claim 13 wherein said volumetric data set depicts a flow of contrast material within a vasculature of the patient over time.

* * * * *